US012685869B2

(12) United States Patent
Spadgenske et al.

(10) Patent No.: US 12,685,869 B2
(45) Date of Patent: Jul. 21, 2026

(54) HEADSET SYSTEM FOR USE WITH IMPLANTED DEVICES

(71) Applicant: Shiratronics, Inc., Brooklyn Park, MN (US)

(72) Inventors: Scott A. Spadgenske, Buffalo, MN (US); Alan H. Smythe, White Bear Lake, MN (US); Kent J. Zehrer, New Hope, MN (US); Scott Anthony Lambert, East Bethel, MN (US); Travis Yoch, Woodbury, MN (US); Robert R. Roberts, III, St. Paul, MN (US)

(73) Assignee: Shiratronics, Inc., Brooklyn Park, MN (US)

( * ) Notice: Subject to any disclaimer, the term of this patent is extended or adjusted under 35 U.S.C. 154(b) by 252 days.

(21) Appl. No.: 18/410,618

(22) Filed: Jan. 11, 2024

(65) Prior Publication Data

US 2024/0238599 A1 Jul. 18, 2024

Related U.S. Application Data

(60) Provisional application No. 63/439,333, filed on Jan. 17, 2023.

(51) Int. Cl.
*A61N 1/05* (2006.01)
*A61N 1/36* (2006.01)
(Continued)

(52) U.S. Cl.
CPC ..... *A61N 1/37235* (2013.01); *A61N 1/37229* (2013.01); *A61N 1/3787* (2013.01); *H02J 50/10* (2016.02); *H02J 50/90* (2016.02)

(58) Field of Classification Search
CPC ............ A61N 1/37235; A61N 1/37229; A61N 1/3787; A61N 1/0529; A61N 1/36075;
(Continued)

(56) References Cited

U.S. PATENT DOCUMENTS 4,065,740 A * 12/1977 Earhart ................... H01F 17/04
336/198
5,862,241 A * 1/1999 Nelson ................. H04R 1/1066
381/374
(Continued)

FOREIGN PATENT DOCUMENTS

WO 2024155508 7/2024

OTHER PUBLICATIONS

"International Application Serial No. PCT US2024 011230, Invitation to Pay Additional Fees mailed May 24, 2024", 8 pgs.
(Continued)

*Primary Examiner* — Carl H Layno
*Assistant Examiner* — Anh-Khoa N Dinh
(74) *Attorney, Agent, or Firm* — Schwegman, Lundberg & Woessner, P.A.

(57) ABSTRACT

A system may include a headset band configured to be worn on a head of a patient, first and second arms, first and second coil assemblies, and at least one power supply electrically connected to the first coil assembly and the second coil assembly. The headset band may include a first end and a second end, and may be configured the first end to be on a first side of the head when the second end is on a second side of the head when worn on the head. The first arm may be rotatably connected to the headset band near the first end, and the second arm may be rotatably connected to the headset band near the second end. The first coil assembly may be connected to the first arm and the second coil assembly may be connected to the second arm.

25 Claims, 34 Drawing Sheets

(51) Int. Cl.

| | |
|---|---|
| *A61N 1/372* | (2006.01) |
| *A61N 1/378* | (2006.01) |
| *H02J 50/10* | (2016.01) |
| *H02J 50/90* | (2016.01) |

(58) Field of Classification Search
CPC .......... H02J 50/10; H02J 50/90; H01Q 1/248; H01Q 1/38; H01Q 7/005; H01Q 9/265
See application file for complete search history.

(56) References Cited

U.S. PATENT DOCUMENTS

| | | | |
|---|---|---|---|
| 6,296,355 B1 * | 10/2001 | Rittmann ............... | G02C 3/003 |
| | | | 351/114 |
| 9,878,170 B2 | 1/2018 | Angara et al. | |
| 9,973,854 B1 * | 5/2018 | Zimmer ................... | A42B 3/30 |
| 2002/0032471 A1 * | 3/2002 | Loftin ................ | A61N 1/37276 |
| | | | 333/32 |
| 2005/0004619 A1 * | 1/2005 | Wahlstrand .......... | A61N 1/3787 |
| | | | 607/45 |
| 2011/0093048 A1 * | 4/2011 | Aghassian ........... | A61N 1/3787 |
| | | | 607/61 |
| 2012/0119699 A1 * | 5/2012 | Carbunaru ............ | H02J 7/0042 |
| | | | 320/108 |
| 2016/0030746 A1 * | 2/2016 | Reed .................. | A61N 1/36075 |
| | | | 607/46 |
| 2017/0135896 A1 * | 5/2017 | Snow ........................ | A61N 1/00 |
| 2017/0223445 A1 * | 8/2017 | Bullen ..................... | H04R 3/04 |
| 2018/0185644 A1 | 7/2018 | Linari et al. | |

OTHER PUBLICATIONS

"International Application Serial No. PCT US2024 011230, International Search Report mailed Jul. 16, 2024", 4 pgs.
"International Application Serial No. PCT US2024 011230, Written Opinion mailed Jul. 16, 2024", 9 pgs.

* cited by examiner 201 201
200 200
204 204
201 201
203

LEFT
IMPLANT

RIGHT
IMPLANT

309

308

310

302

15E

15E

1557

1557

1563

1561

1562

1560

1559

1564

1558

1566

1565

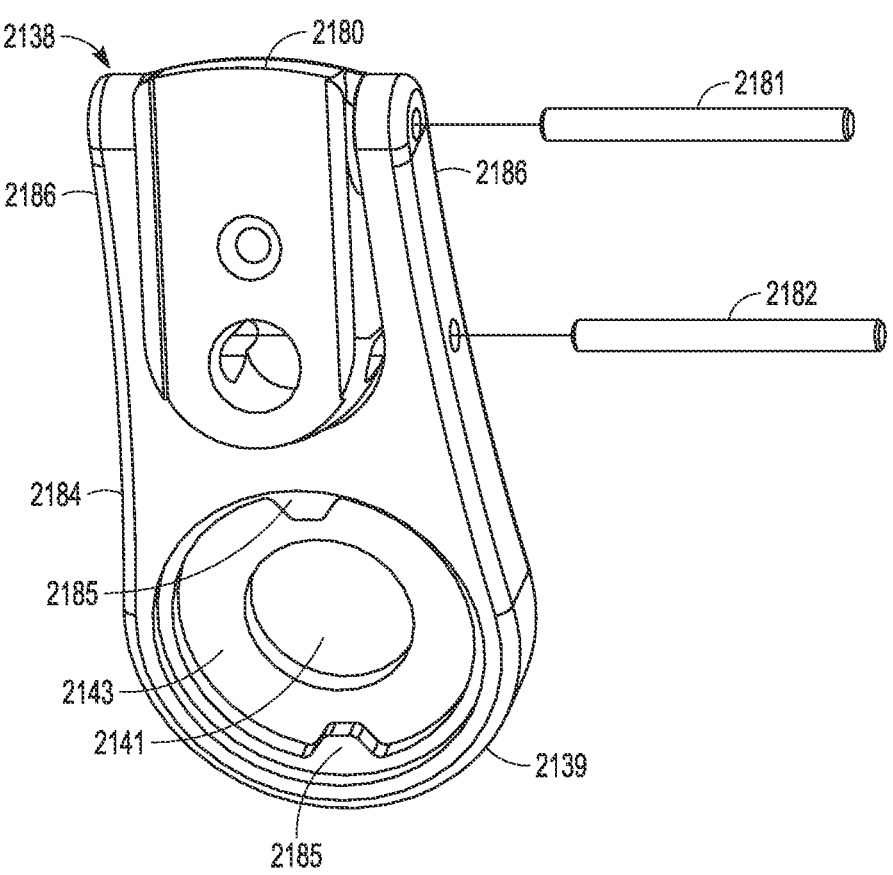
FIG. 21
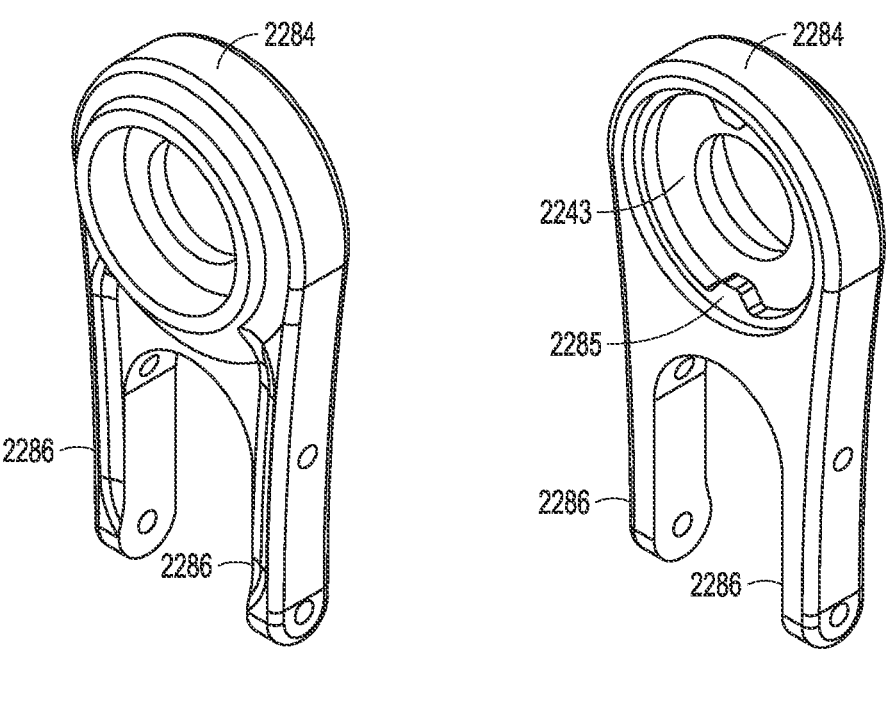
FIG. 22A                    FIG. 22B

FIG. 25A                 FIG. 25B

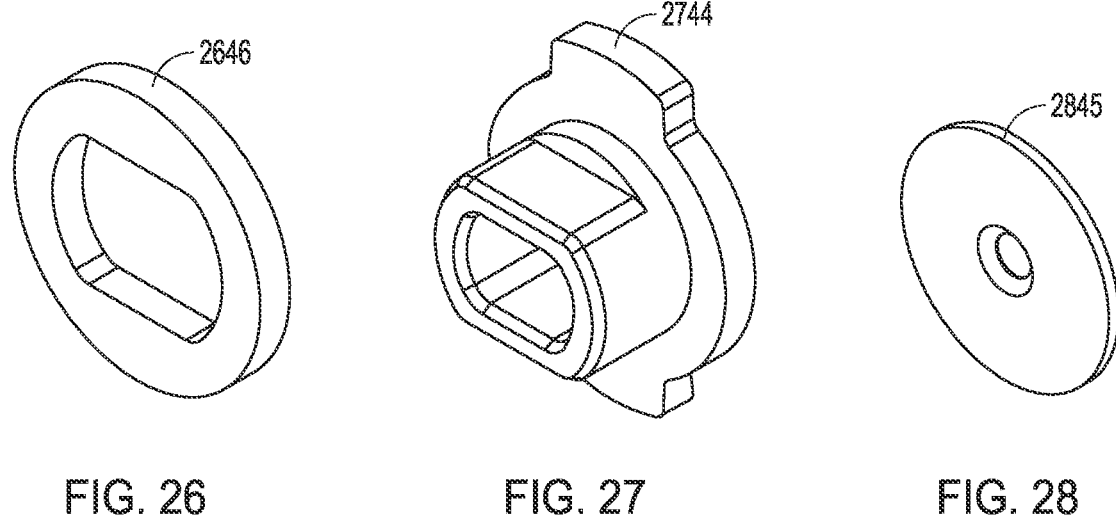
FIG. 26          FIG. 27          FIG. 28
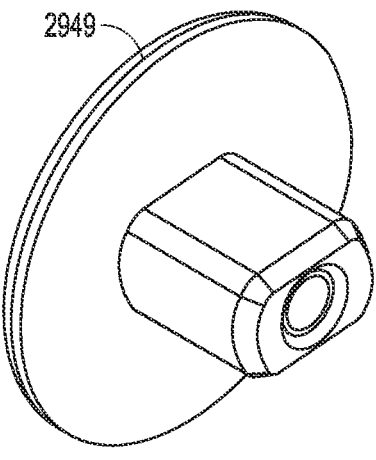
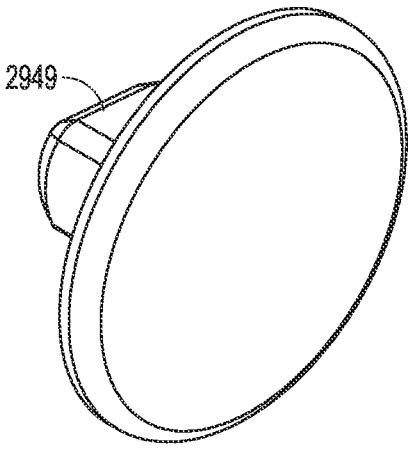
FIG. 29A          FIG. 29B

HEADSET SYSTEM FOR USE WITH IMPLANTED DEVICES

PRIORITY

This application claims the benefit of priority to U.S. Provisional Patent Application Ser. No. 63/439,333, filed Jan. 17, 2023, which is incorporated by reference herein in its entirety.

TECHNICAL FIELD

This document relates generally to medical systems, and more particularly, but not by way of limitation, to headset systems, devices, and methods for use to charge and/or communicate with head-located implantable devices.

BACKGROUND

Medical devices may include implantable devices configured to deliver a therapy, such as but not limited to an electrical therapy and/or to sense electrical signals to detect physiological or functional parameters or other health-related data. Implantable neurostimulators are a specific example of implantable electrical therapy devices. A fully head-located implantable peripheral neurostimulation system, having one or more implantable devices, designed for the treatment of chronic head pain is a specific example of an implantable neurostimulation system.

The shape and size of the human bead, in which the fully head-located implantable device(s) are located, is variable from patient to patient. Furthermore, the human head is not symmetric. These variations make it difficult to use a coil for charging devices implanted in the head and/or communicating with devices implanted in the head.

SUMMARY

An example (e.g., "Example 1") of a system may include a headset band configured to be worn on a head of a patient, first and second arms, first and second coil assemblies, and at least one power supply electrically connected to the first coil assembly and the second coil assembly. The headset band may include a first end and a second end, and may be configured the first end to be on a first side of the head when the second end is on a second side of the head when worn on the head. The first arm may be rotatably connected to the headset band near the first end, and the second arm may be rotatably connected to the headset band near the second end. The first coil assembly may be connected to the first arm and the second coil assembly may be connected to the second arm.

In Example 2, the subject matter of Example 1 may optionally be configured such that the at least one power supply includes a charger device connected to the first coil assembly by a first set of conductors in a cable and connected to the second coil assembly by a second set of conductors in the cable.

In Example 3, the subject matter of Example 2 may optionally be configured such that the charger device includes at least one indicator configured to indicate when the first coil assembly is operably aligned with a first implantable device and indicate when the second coil assembly is operably aligned with a second implantable device.

In Example 4, the subject matter of Example 3 may optionally be configured such that the at least one indicator includes a first light and a second light on an exterior of the charger device, the first light corresponding to alignment of the first coil assembly and the second light corresponding to alignment of the second coil assembly.

In Example 5, the subject matter of any one or more of Examples 3-4 may optionally be configured such that the system is configured to determine alignment based on reflected impedance.

In Example 6, the subject matter of any one or more of Examples 3-5 may optionally be configured such that the system is configured to determine alignment based on communication capability with the first and second implantable devices.

In Example 7, the subject matter of any one or more of Examples 1-6 may optionally be configured such that the headset band has a flexible arcuate shape and has an ability to retain shape. The headset band may be configured to be expanded to further separate the first and second ends when the headset band is applied to the head and allow the ability to retain shape to provide opposing forces for the first and second ends toward the head.

In Example 8, the subject matter of any one or more of Examples 1-7 may optionally be configured such that each of the first and second arms may include a connection portion and a coil portion. The connection portion of the first arm may be rotatably connected to the headset band near the first end, and the connection portion of the second arm is rotatably connected to the headset band near the second end. The first coil assembly may be connected to the coil portion of the first arm, and the second coil assembly may be connected to the coil portion of the second arm.

In Example 9, the subject matter of Example 8 may optionally be configured such that each of the first and second arms has a bend between the coil portion and the connection portion.

In Example 10, the subject matter of any one or more of Examples 8-9 may optionally be configured such that each of the first and second arms is flexible and has an ability to retain shape.

In Example 11, the subject matter of Example 10 may optionally be configured such that each of the first and second arms further has a temple portion. The connection portion may be between the temple portion and the coil portion.

In Example 12, the subject matter of Example 11 may optionally be configured such that each of the first and second arms has a bend between the temple portion and the connection portion and a bend between the connection portion and the coil portion such that the first and second arms curve inward toward the head when worn on the head.

In Example 13, the subject matter of any one or more of Examples 1-12 may optionally be configured to further include a first arm bracket and a second arm bracket. The first arm bracket may be configured to rotatably connect the first arm to the headset band and the second arm bracket may be configured to rotatably connect the second arm to the headset band.

In Example 14, the subject matter of Example 13 may optionally be configured such that each of the first and second arm brackets includes a first bracket end portion and a second bracket end portion and an aperture extending therethrough at the first bracket end portion for a fastener to extend through to connect to the headset band.

In Example 15, the subject matter of Example 14 may optionally be configured such that the first bracket end portion includes a recess with the aperture extending through the recess. The arm bracket may include a bearing configured to fit within the recess. The first bracket end portion may include a feature in the recess to engage with a feature in the bearing to limit rotational motion of the arm.

In Example 16, the subject matter of any one or more of Examples 14-15 may optionally be configured to further include a spring between the headset band and the first bracket end portion to provide some resistance to rotation with respect to the headset band.

In Example 17, the subject matter of any one or more of Examples 14-16 may optionally be configured such that the second bracket end portion includes a pivot portion config-ured to pivot about a pivot pin at the second bracket end portion. The second bracket portion may be configured to be attached to the connection portion of a respective one of the first and second arms.

In Example 18, the subject matter of Example 17 may optionally be configured such that the second bracket por-tion includes a stop pin configured to limit pivoting motion of the pivot portion about the pivot pin.

In Example 19, the subject matter of any one or more of Examples 17-18 may optionally be configured such that each of the first and second arm brackets includes a spring configured to provide a force against the pivot portion.

In Example 20, the subject matter of any one or more of Examples 2-19 may optionally be configured such that the first coil assembly and the first arm are configured for the first coil assembly to slide over an end of the first arm, and the second coil assembly and the second arm are configured for the second coil assembly to slide over an end of the second arm.

In Example 21, the subject matter of Example 20 may optionally be configured such that the end of the first arm and the end of the second arm each have a bent end portion. The bent end portion is sufficiently flexible to allow a user to apply force to intentionally slide a corresponding one of the first coil assembly and the second coil assembly past the bent end portion on or off of the corresponding arm, while the corresponding one of the first coil assembly and the second coil assembly remain in place under normal use.

In Example 22, the subject matter of Example 20 may optionally be configured such that the end of the first arm and the end of the second arm each have a stopper config-ured to be removably attached to the end. A corresponding one of the first coil assembly and the second coil assembly may be able to slide over the end when the stopper is removed, and is not able to slide over the end when the stopper is attached.

In Example 23, the subject matter of any one or more of Examples 1-22 may optionally be configured such that each of the first and second coil assemblies includes a coil housing with a recessed central portion and a post, a spring around the post, and a headset housing pivot connected to the post. The spring may apply a force between the headset housing pivot and the coil housing. The coil housing and the headset housing pivot may be configured to allow limited tilting motion of the headset housing pivot on the post.

In Example 24, the subject matter of any one or more of Examples 1-23 may optionally be configured such that each of the first and second coil assemblies includes an outer coil housing ultrasonically welded to an inner coil housing to form a coil housing, and includes a coil electrically con-nected to a printed circuit board assembly (PCBA) within the coil housing.

In Example 25, the subject matter of any one or more of Examples 1-23 may optionally be configured such that each of the first and second coil assemblies includes a strain relief between an outer coil housing and an inner coil housing. The strain relief may be configured to relieve strain for an electrically conducting cable. The housing and the strain relief may be configured to provide a tongue and groove fit between the strain relief and each of the outer coil housing and the inner coil housing.

In Example 26, the subject matter of any one or more of Examples 1-25 may optionally be configured such that each of the first and second coil assemblies has a concave surface directed toward the head when worn on the head, and the concave surface is configured to assist with alignment over an implantable medical device.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodi-ments are demonstrative and not intended to be exhaustive or exclusive embodiments of the present subject matter.

FIG. 21 illustrates, by way of example and not limitation, a partially-exploded view of the arm bracket with the pivot pin and stop pin being inserted.

FIGS. 22A-22B illustrate, by way of example and not limitation, front and rear perspective views of the bracket frame.

FIG. 26 illustrates, by way of example and not limitation, the D-shaped washer.

FIG. 27 illustrates, by way of example and not limitation, the bearing.

FIG. 28 illustrates, by way of example and not limitation, the washer.

FIGS. 29A-29B illustrate, by way of example and not limitation, the outer pivot.

DETAILED DESCRIPTION

Figure 1A:
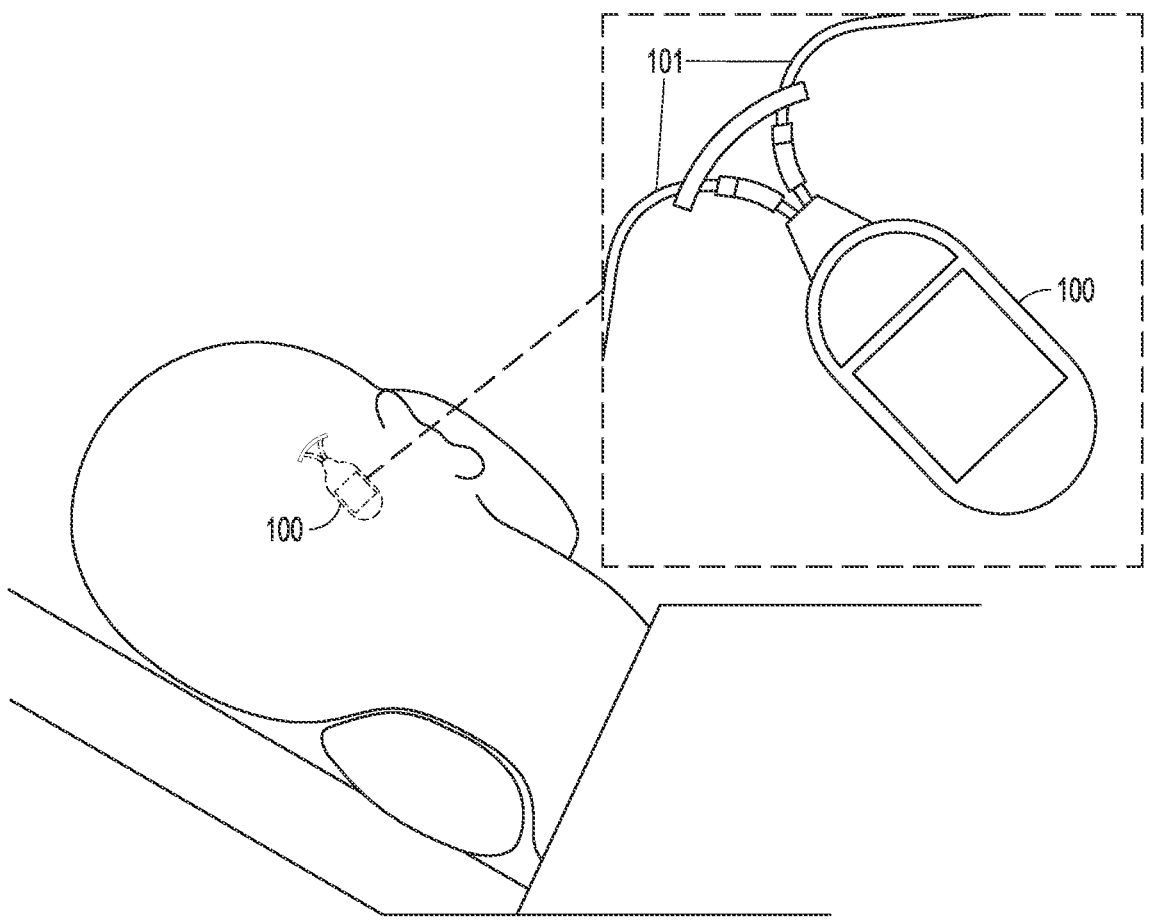
FIGS. 1A-1B illustrate, by way of example and not limitation, a system that includes implantable medical device(s) and an external device configured for use to communicate with and charge the implantable medical device(s).

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A coil may be used to communicate with an implantable device and/or charge the implantable device by properly aligning the coil within a close enough proximity to the implanted device to provide the communication and/or charging functions. However, there are significant challenges with using a coil to communicate with device(s) and/or charge the device(s) that are implanted in the head because the shape and size of the head is variable and the head is not symmetric from side to side. Multiple devices further complicate the process because several coils need to be properly positioned within proximity of the device and properly aligned with the device for a sufficient amount of time to perform the recharge process and/or communication process.

Various embodiments of the present subject matter provide an external coil system with the ability to align coils with implantable devices within range of the implantable devices, and to maintain the alignment and position while allowing the user to comfortably move without disrupting the communication or charging process. The external coil system may be a wearable system, such as a headset configured to adjustably position and align coil(s) to their respective implanted device(s). As the required time for alignment may range from minutes to several hours to perform the communication process and/or recharge process, various embodiments of the external system should allow a patient to be able to place the recharge coil(s) within proximity of the implantable device and secure the coil(s) in place for long periods of time.

Various embodiments of the present subject matter provide an external coil system configured to be used with more than one implanted device by simultaneously placing the coils in alignment with their respective implanted device. The external coil system may be designed to be comfortably used by the patient, allowing the patient to freely move and adjust their posture without significant disruption to the charging and/or communication process. For example, the external coils system may be a headset configured to be comfortably worn while performing charging and/or communication processes with head-located implanted devices. The external coils system may be configured to accommodate varying anatomy, including different external skull features such as width, length, and height of skull, location of various anatomy landmarks such as ears, temples and support varying thickness of head hair, hairlines, and no hair or bald heads.

Various external coil systems may be configured to enable the patient to independently manipulate individual charging coils to position and align the coils correctly over their respective implantable device. The external coils may be able to move in a 3-dimension space such that both large movements can be accommodated along with small adjustments of each coil in x, y, and z directions. The external coil system should be able to hold the coil in place and alignment for long periods of time on the order of minutes and up to several hours to perform the communication and/or charging process. The external coil system may further be configured to notify the patient when correct alignment is achieved.

Various embodiments of the present subject matter provide a mechanical adjustable headset system that enables a patient to quickly locate and align communication coils over more than one implanted device, and thereby providing an efficient comfortable charging process that allows the patient to easily adjust coil location and alignment while accommodating patient anatomy variations while offering the patient a full range of movement In each of the solutions the coils are managed and connect to a charger that may include status information regarding state of charge for the implantable device or alignment information of coils. Each coil may be placed on a movable arm to accommodate movement in x, y, and z directions and accommodate the varying human head anatomy. The flexibility of the movable arm allows the patient to locate the implantable device and align the external coil over the implantable coils. The coil(s) may be connected to an external device (e.g., charger), which may be configured to provide status information such as alignment information. The status information may include other information such as a status (e.g., battery charge status) of the implantable device and/or the external charger.

Figure 1B:
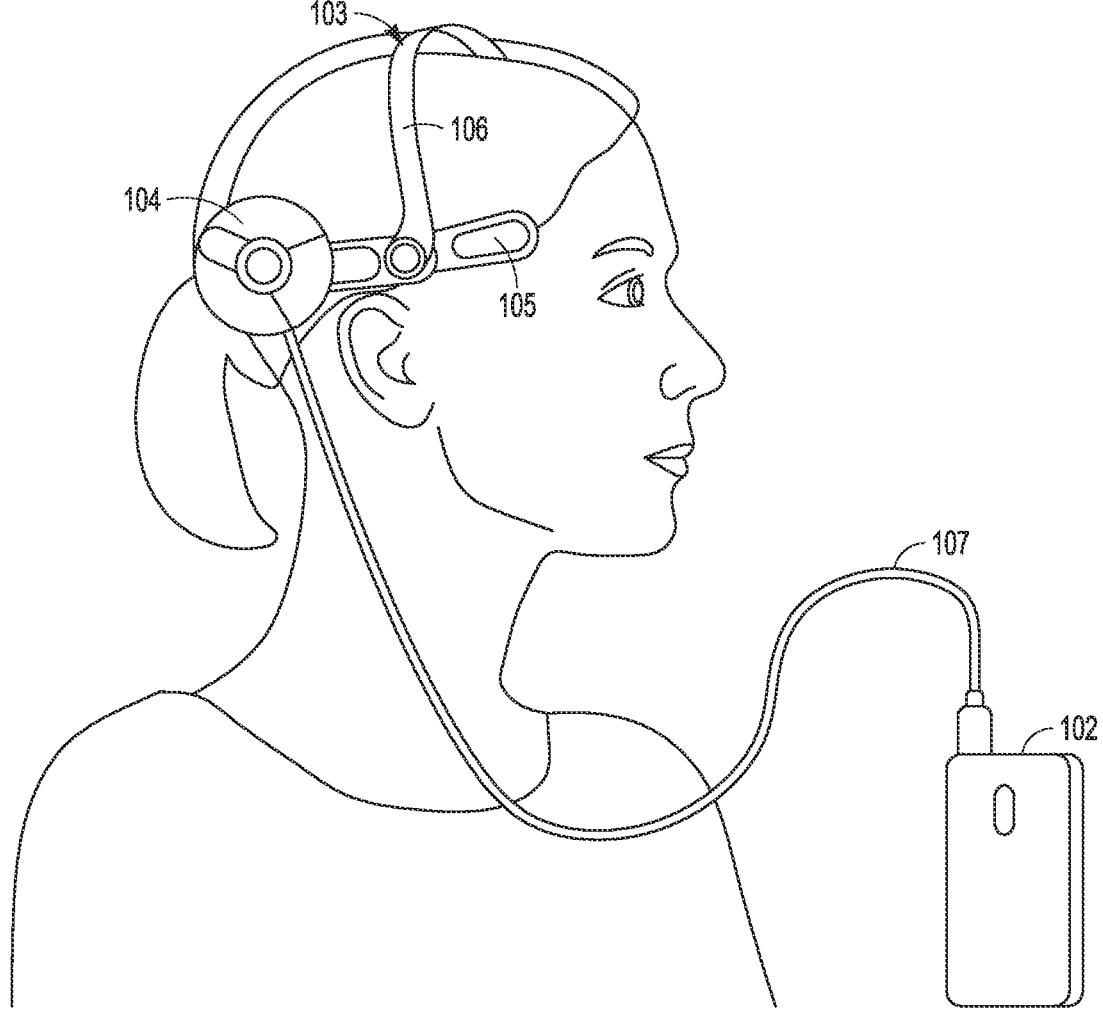

FIGS. 1A-1B illustrate, by way of example and not limitation, a system that includes implantable medical device(s) and an external device configured for use to communicate with and charge the implantable medical device(s). More particularly, the system is an example of a fully head-located neurostimulation system designed for the treatment of chronic head pain. The system may be configured to provide neurostimulation therapy for chronic head pain, including chronic head pain caused by migraine and other headaches, as well as chronic head pain due other etiologies. For example, the system may be used to treat chronic head and/or face pain of multiple etiologies, including migraine headaches; and other primary headaches, including cluster headaches, hemicrania continua headaches, tension type headaches, chronic daily headaches, transformed migraine headaches; further including secondary headaches, such as cervicogenic headaches and other secondary musculoskeletal headaches; including neuropathic head and/or face pain, nociceptive head and/or face pain, and/or sympathetic related head and/or face pain; including greater occipital neuralgia, as well as the other various occipital neuralgias, supraorbital neuralgia, auriculotemporal neuralgia, infraorbital neuralgia, and other trigeminal neuralgias, and other head and face neuralgias.

FIG. 1A illustrates an implantable medical device 100 implanted beneath the skin and over a patient's cranium. The device 100 is illustrated as being implanted behind and above the ear. The implantable medical device 100 may include one or more leads 101 that may be subcutaneously tunneled to a desired neural target. Each lead may include one or more electrodes. The number of electrodes and spacing may be such as to provide therapeutic stimulation over any one or any combination of the supraorbital, parietal, and occipital region substantially simultaneously. The implantable medical device 100 may be configured to independently control each electrode to determine whether the electrode will be inactive or configured as a cathode or an anode. One or more electrodes on the lead(s) may be configured to function as an anode, and one or more electrodes on the lead may be configured to function as a cathode. For example, bipolar neuromodulation may be delivered using one or more anodes and one or more cathodes on the lead(s). A clinician may program the electrode configurations to provide a neuromodulation field that captures a desired neural target for the therapy.

FIG. 1B illustrates an external device 102 and headset 103 configured for use to communicate with and/or charge the implantable medical device(s) 100. The headset 103 may include an external coil 104, and the headset 103 may be configured to position the external coil over an implantable medical device. For example, the headset 103 may include an adjustable frame 105 on each side of the head that can rotate about a point on a main headset frame 106, and may be configured to provide additional degrees of motion (e.g., sliding or pivoting motion) with respect to the main headset frame 106. These adjustable frames may be used to position the external coils 104 over the implantable medical devices 100 when the main headset frame 106 is worn. The external device 102 may be electrically connected to the external coil 104 via a cable 107. In some embodiments, the external device 102 may be wirelessly connected to the headset 103. The headset may be configured to wirelessly receive power from the external device and to transfer power and provide communications from the external coil to the implanted device(s).

Figure 2:
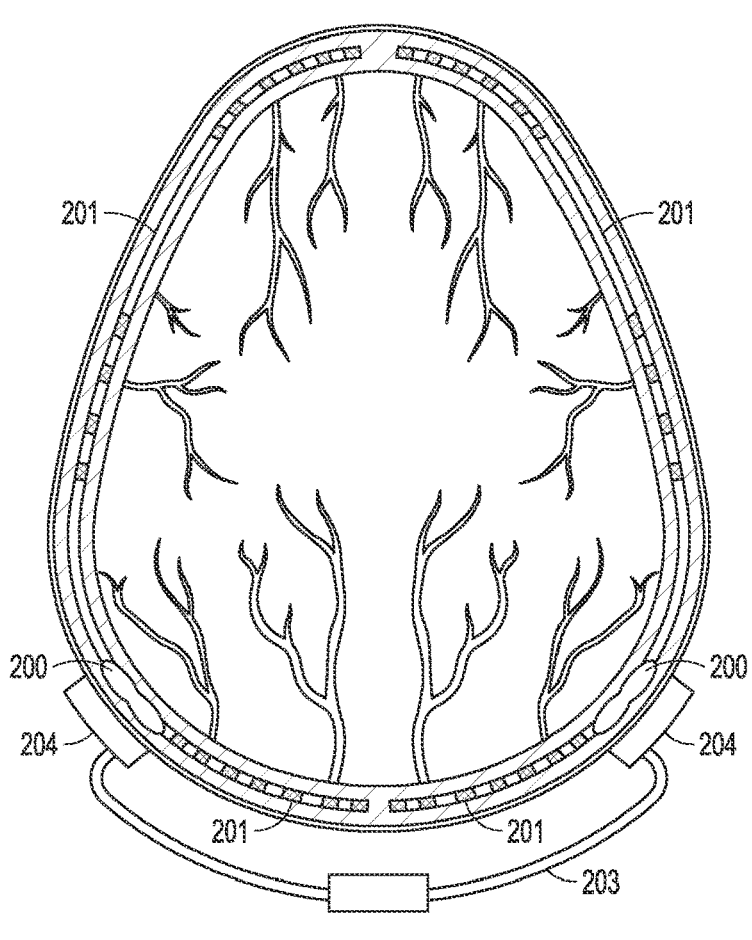
FIG. 2 illustrates, by way of example and not limitation, two implanted devices with leads to cover both sides of the head with one of the devices on the left side of the head and the other on the right side of the head, and a charging/communication headset disposed about the cranium.

FIG. 2 illustrates, by way of example and not limitation, two implanted devices 200 with leads 201 to cover both sides of the head with one of the devices on the left side of the head and the other on the right side of the head, and a charging/communication headset 203 disposed about the cranium. The headset 203 may include right and left coupling coil enclosures 204, respectively that contain coils for coupling to the respective coils in the implants. The coil enclosures 204 may interface with a main charger/processor body which may contain processor circuitry and batteries for both charging the internal battery in the implantable medical devices 200 and also communicating with the implanted devices. Thus, in operation, when a patient desires to charge their implanted devices 200, all that is necessary for some embodiments is to place the headset about the cranium with the coils 204 in close proximity to the respective implanted devices 200. In some embodiments, such placement may automatically initiate charging; whereas in other embodiments, the user may initiate charging using an external device. When the headset 203 is worn by a patient, the headset coils (transmit coils) 204 are placed in proximity to the corresponding receive coil in each respective body-implanted implantable medical device 200. The headset 203 may include telemetry circuitry, a controller, a battery, and a Bluetooth wireless interface. The headset 203 may also communicate with a personal device such as a smartphone or tablet (e.g., via the Bluetooth interface), for monitoring and/or programming operation of the two implantable medical devices.

The implantable medical device 200 may include a rechargeable battery, an antenna (e.g., coil), and at least one Application Specific Integrated Circuit (ASIC), along with the necessary internal wire connections amongst these related components, as well as to the incoming lead internal wires. These individual components may be encased in a can made of a medical grade metal, which may be encased by plastic cover. The battery may be connected to the ASIC(s) via a connection that is flexible. The overall enclosure for the battery, antenna and ASIC(s) may have a very low flat profile with two lobes, one lobe for housing the ASIC(s) and one lobe for housing the battery. The antenna may be housed in either of the lobes or in both lobes. The use of the two lobes and the flexible connection between the ASIC(s) and the battery allows the implanted device to conform to the shape of the human cranium when subcutaneously implanted without securing such to any underlying structure with an external fixator.

The ASIC(s) and lead(s) may be configured to independently drive each of the electrodes using a neuromodulation signal in accordance with a predetermined program. The programmed stimulation may be defined using parameters such as one or more pulse amplitudes, one or more pulse widths and one or more pulse frequencies. Other parameters may be used for other defined waveforms, which may but does not necessarily use rectilinear pulse shapes. Once the program is loaded and initiated, a state machine may execute the particular programs to provide the necessary therapeutic stimulation. The ASIC(s) may have memory and be configured for communication and for charge control when charging a battery. Each of the conductors in the leads interface with the ASIC(s) such that the ASIC(s) individually controls each conductor in each lead. Thus, each electrode may be individually controlled. Each electrode may be individually turned off, or as noted above, each electrode can be designated as an anode or a cathode. During a charging operation, the implanted device is interfaced with an external charging unit via the antenna (e.g., coil) which is coupled to a similar antenna (e.g., coil) in the external charging unit. Power management involves controlling the amount of charge delivered to the battery, the charging rate thereof and protecting the battery from being overcharged.

The ASIC(s) may be capable of communicating with an external unit, typically part of the external charging unit, to exchange information. Thus, configuration information can be downloaded to the ASIC and status information can be retrieved. A headset may be provided for such external charging/communication operation.

Figure 3:
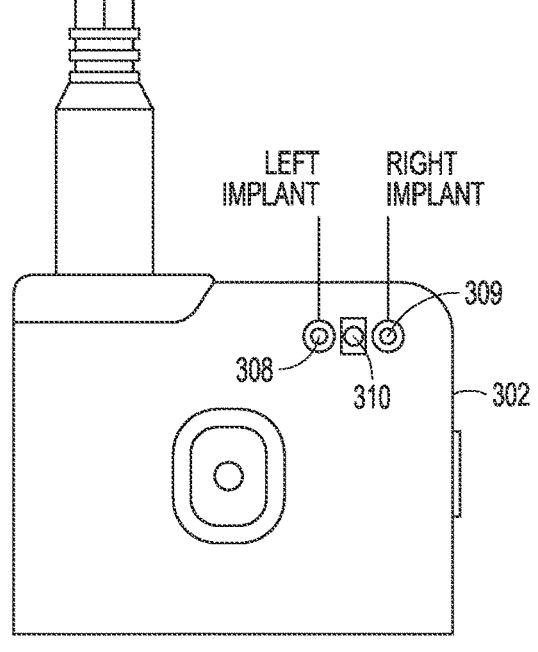
FIG. 3 illustrates, by way of example and not limitation, an external device configured to be connected to a headset to energize the coils in the headset to charge the implantable medical devices and/or to communicate with the implantable medical devices via the coils.

FIG. 3 illustrates, by way of example and not limitation, an external device 302 configured to be connected to a headset, such as headset 103 in FIG. 1B or headset 203 in FIG. 2, to energize the coils in the headset to charge the implantable medical devices and/or to communicate with the implantable medical devices via the coils. The connection between the headset and the external device may be a wired connection such as provided by a cable or a wireless connection. The external device may be referred to as a charger for embodiments in which the external device is used to charge the implantable medical devices. The external device may also communicate with a personal device such as a smartphone or tablet (e.g., via the Bluetooth interface), for monitoring and/or programming operation of the two implantable medical devices, and/or may communicate through a network to remote computers for monitoring and/or programming purposes. As illustrated in FIG. 3, the external device (e.g., charger) 302 may include separate indicators for each of the implanted devices. For example, a left light 308 may provide an indication of the alignment of the left coil with the left implanted device, and a right light 309 may provide an indication of the alignment of the right coil with the right implanted device. Some embodiments may light the indicator when the coil is adequately aligned with the respective device. Some embodiments may use different color lights to indicate how close the external coil is to being adequately aligned with the implantable device coil. Other indicator technology may be used. For example, some embodiments may use haptic information (such as but not limited to vibration pattern(s)) to indicate when the coil is adequately aligned or indicate how close the coil is to being adequately aligned. Some embodiments may use sound (including tones or voice messages) to indicate when the coil is adequately aligned or indicate how close the coil is to being adequately aligned. Some embodiments may include a display screen to provide visual indicators to indicate whether each coil is adequately aligned, and in some embodiments how close the coils are to being adequately aligned. The system may make the alignment determination based simply on whether the external device can communicate with the implantable device through the coil. In some embodiments, the system may determine a measure indicative of transferred energy from the external coil to the implantable coil to indicate whether the coil is adequately aligned and determine how close the coil is to being adequately aligned. For example, some embodiments measure the reflected impedance that is based on the inductive coupling between the external coil and the implantable device coil.

The external device may also provide other types of indicator(s) 310. For example, the other indicator(s) may be for the implantable device(s) and the external device. For example, the external device may provide an indicator of how much charge is in a rechargeable battery in each of the implantable device(s), an indicator of how much charge is in a battery (rechargeable or non-rechargeable) of the external device, an indicator of whether the external device is On or Off, an indicator of whether the external device is currently charging the implantable device(s), or an indicator of a connection to a personal device (e.g., a wireless connection via Wi-Fi or Bluetooth to a phone or tablet).

Figure 4A:
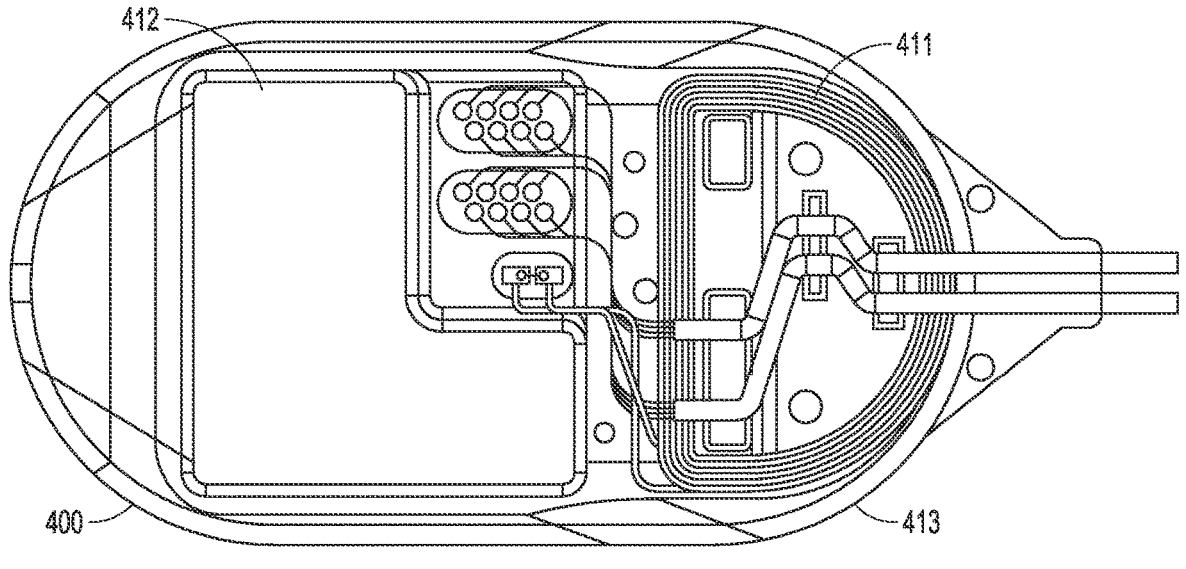
FIGS. 4A-4C illustrate, by way of example and not limitation, an implantable medical device.
Figure 4B:
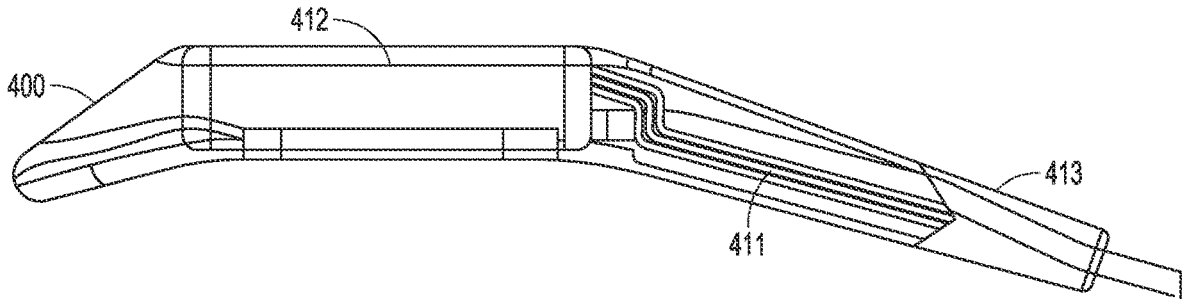
Figure 4C:
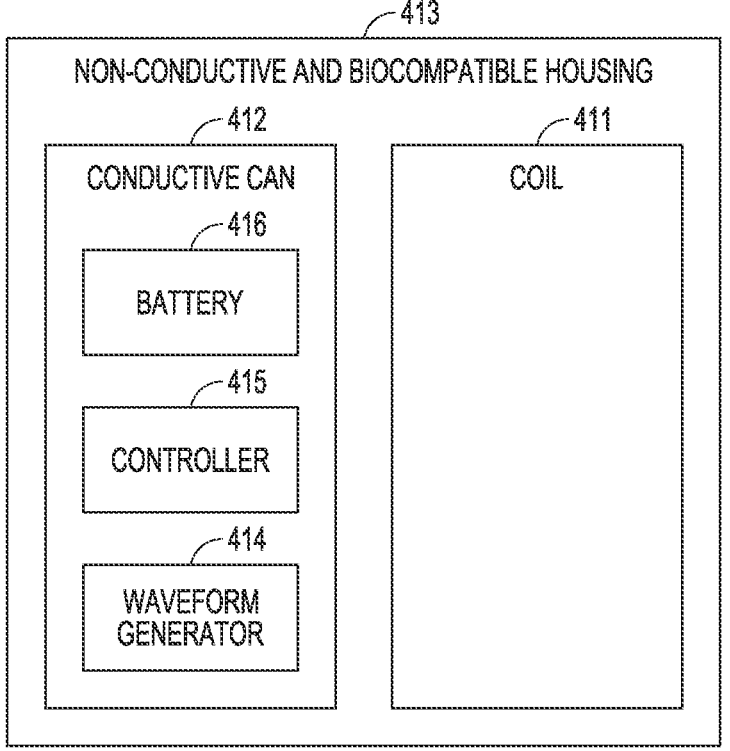

FIGS. 4A-4C illustrate, by way of example and not limitation, an implantable medical device. The illustrated device 400 is configured for implantation under the skin but over bone, muscle or other tissue such as cartilage. For example, the illustrated device may be subcutaneously implanted over a cranium. The device 400 includes a coil 411 used for communication and charging, a conductive enclosure 412 (e.g., metal can) for electronics, and a non-conductive and biocompatible coating 413 that encases the conductive enclosure 412 and the coil 411. The electronics within the conductive enclosure may include a neurostimulator waveform generator 414, a controller 415 and a battery 416. At least one microcontroller unit (MCU) and/or at least one application specific integrated circuit (ASIC) may provide the controller and the neurostimulator waveform generator functions. The MCU(s) may contribute to one or both of the controller and the neurostimulator waveform generator functions. The ASIC(s) may contribute to one or both of the controller and the neurostimulator waveform generator functions. The MCU(s) and/or ASIC(s) may be encased within the conductive enclosure. The coil is not within the conductive enclosure, so that it can be used to perform charging and communication functions using an electromagnetic field. The non-conductive housing may include silicone or an epoxy. Also, the non-conductive housing is a poor conductor of heat, and thus insulates the tissue from any heat generated at the coil or the conductive enclosure. The housing may be flexible, allowing some motion or flex when implanted, which encourages a low profile as it follows a curvature of a cranium when subcutaneously implanted over the cranium.

The illustrated housing may include a first housing portion and a second housing portion, where the first housing portion encapsulates the coil and the second housing portion encapsulates the conductive housing (e.g., metal can). The first and second housing portions may have substantially equal footprints. Each of the first and second housing portions have a thickness, length and width. The thickness may be uniform and may be less than the length and the width. Each of the first and second housing portions may have a substantially planar major surface, wherein the first and second housing portions are joined such that the substantially planar major surfaces form an angle between 90 degrees and 180 degrees. This angle allows the substantially planar major surfaces for the first and second housing portions to follow the curvature of the cranium. Another lobe may be included, which may encourage the implanted device to remain in place when implanted as it provides the implantable medical device with a profile that follows the curvature of the cranium.

Figure 5:
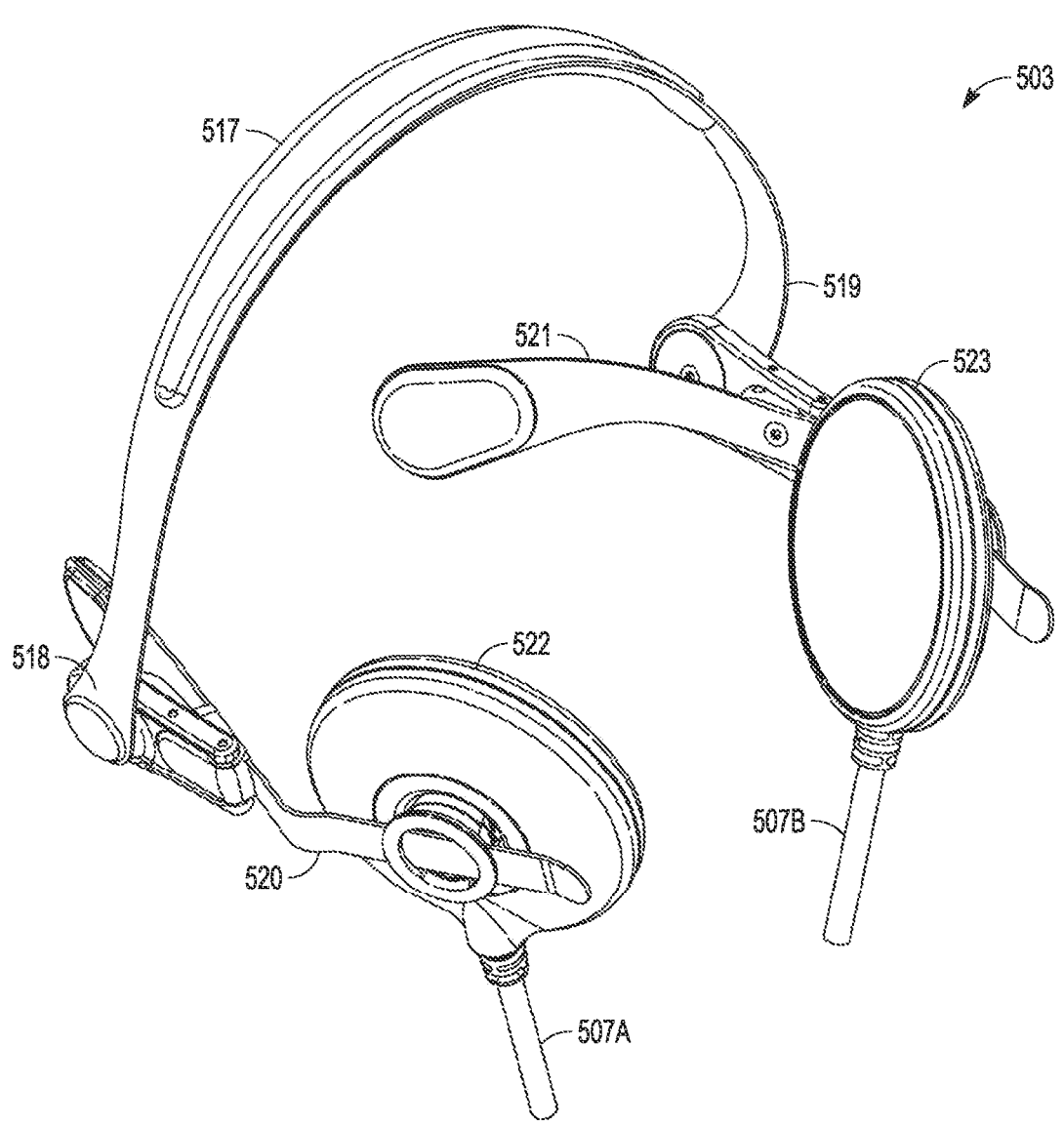
FIG. 5 illustrates, by way of example and not limitation, a headset.

FIG. 5 illustrates, by way of example and not limitation, a headset 503, similar to the headset 103 illustrated in FIGS. 1A-1B. The illustrated headset 503 includes a headset band 517 configured to be worn on a head of a patient. The headset band 517 has a first end 518 and a second end 519. When worn on the head, the first end 518 of the headset band 517 is on a first side of the head and the second end 519 of the headset band 517 is on a second side of the head. The headset 503 includes a first arm 520 rotatably connected to the headset band 517 near the first end 518, and a second arm 521 rotatably connected to the headset band 517 near the second end 519. The headset 503 further includes a first coil assembly 522 connected to the first arm, and a second coil assembly 523 connected to the second arm. For example, the coil assemblies 522, 523 may be slid over an end of the arms 520, 521, or otherwise removably attached to the arms. At least one power supply may be electrically connected to the first coil assembly and the second coil assembly. The external device (e.g., charger) 102, 302 in FIG. 1B and FIG. 3 may provide the electrical power to the coil assemblies via a cable, illustrated as a bifurcated cable portions 507A and 507B to make individual connections to each coil assembly 522, 523.

Figure 6:
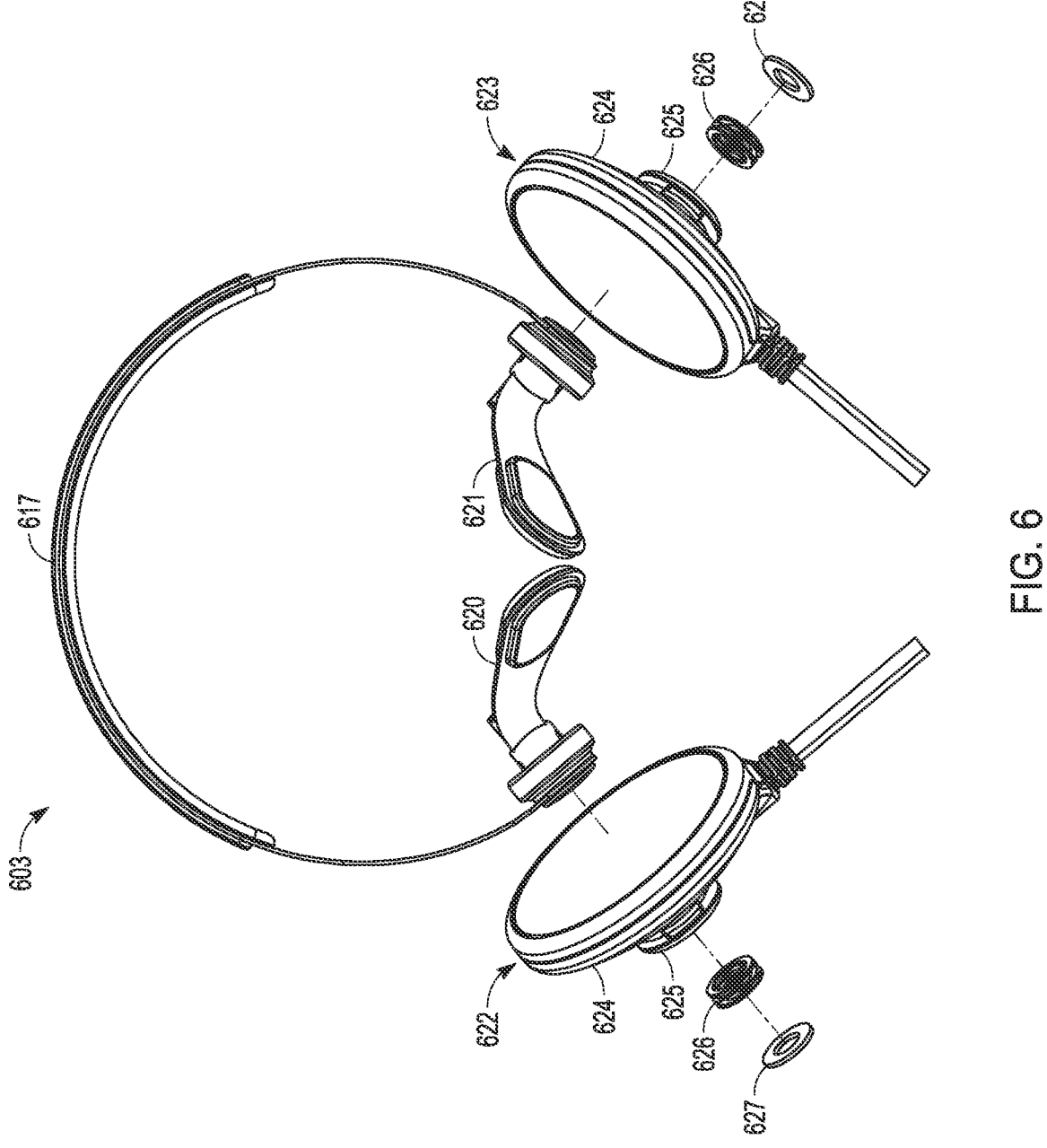
FIG. 6 illustrates, by way of example and not limitation, a partially-exploded view of the attachment of the coil assemblies to the arms of the headset.

FIG. 6 illustrates, by way of example and not limitation, a partially-exploded view of the attachment of the coil assemblies to the arms of the headset. Similar to FIG. 5, the illustrated headset 603 includes a headset band 617, a first arm 620 rotatably connected to the headset band 617, a second arm 621 rotatably connected to the headset band 617, a first coil assembly 622 connected to the first arm 620, and a second coil assembly 623 connected to the second arm 621. A spring 626 (e.g., a wave spring) and washer 627 fit within a connector portion 625 of the coil housing 624, and are used to provide friction to keep the coil in place when moved. The amount of friction provided by the spring and washer avoid the coil from unintentionally sliding along the arm during normal use, but still allow a user to intentionally move the coil along the arm with relative ease. By way of example and not limitation, the coil may be retained by a bent tab (also referred to as a bent end portion) at the end of the arm (see FIG. 8).

Figure 7:
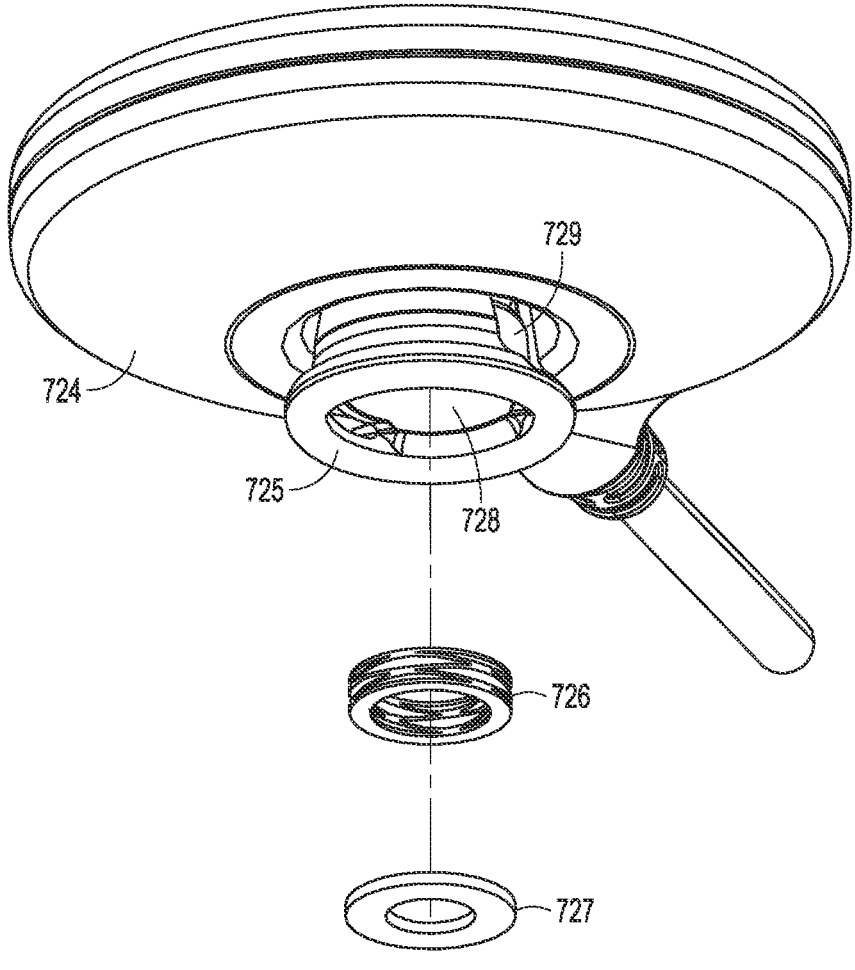
FIG. 7 illustrates, by way of example and not limitation, a closer exploded view of the connector portion of the coil housing, similar to the partially-exploded view of FIG. 6.

FIG. 7 illustrates, by way of example and not limitation, a closer exploded view of the connector portion 725 of the coil housing 724, similar to the partially-exploded view of FIG. 6. The connector portion 725 may be central cylindrical-like structure with an open end 728 through which the wave spring and the washer may be inserted. The sidewalls of the cylindrical-like structure may have apertures 729 through which an end of the arm may be inserted. The spring 726 pushes the washer 727 into the arm which has been inserted through the apertures 729, which provides a friction fit for the coil assembly on the arm. The coil housing 724 may have a recessed central portion and a post, and a spring around the post. The connector portion 725 may be connected to the post in a manner to allow limited tilting motion, and in some embodiments rotational motion, of the connector portion 725 with respect to the coil housing 724. FIGS. 36-38C (see the headset housing pivot), discussed in detail below, illustrates an example of the connector portion 725.

Figure 8:
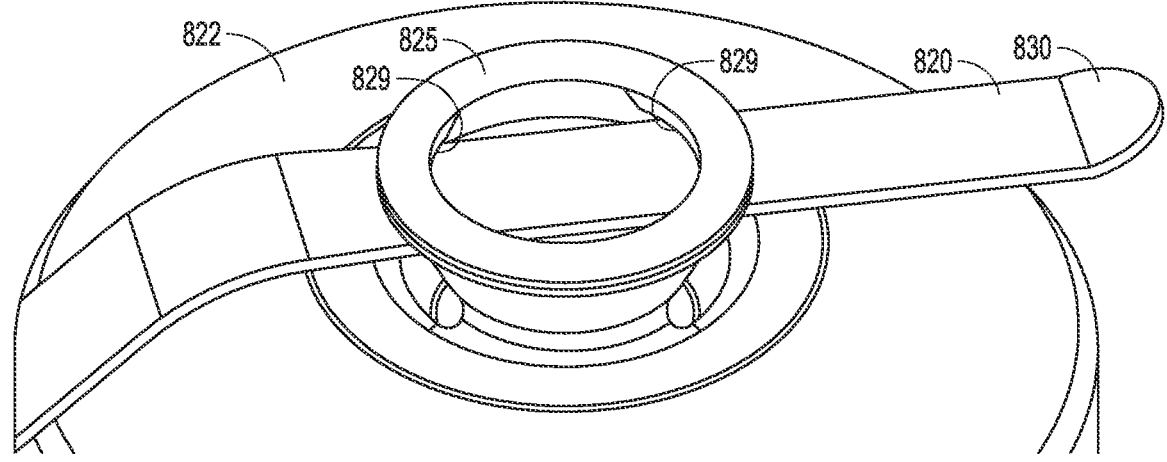
FIG. 8 illustrates, by way of example and not limitation, an arm extending through apertures in the side wall of the connector portion.

FIG. 8 illustrates, by way of example and not limitation, an arm 820 extending through apertures 829 in the side wall of the connector portion 825. The arm 820 has a bent end portion 830 designed to keep the coil assembly 822 on the arm 820. The bent end portion has ability to retain shape and has sufficient flexibility to allow the connector portion 825 to be slid onto the arm 820 and then return to a shape that prevents the coil assembly 822 from sliding off the arm without intentional effort by a user to remove it. The spring and washer are inside of the connector portion 825 and are hidden by the arm 820. The spring and washer provide sufficient force against the arm 820 to allow the coil assembly 822 to remain in place on the arm 820, while allowing the user to adjust the position of the coil assembly 822 along the arm 820 with relative ease.

Figure 9:
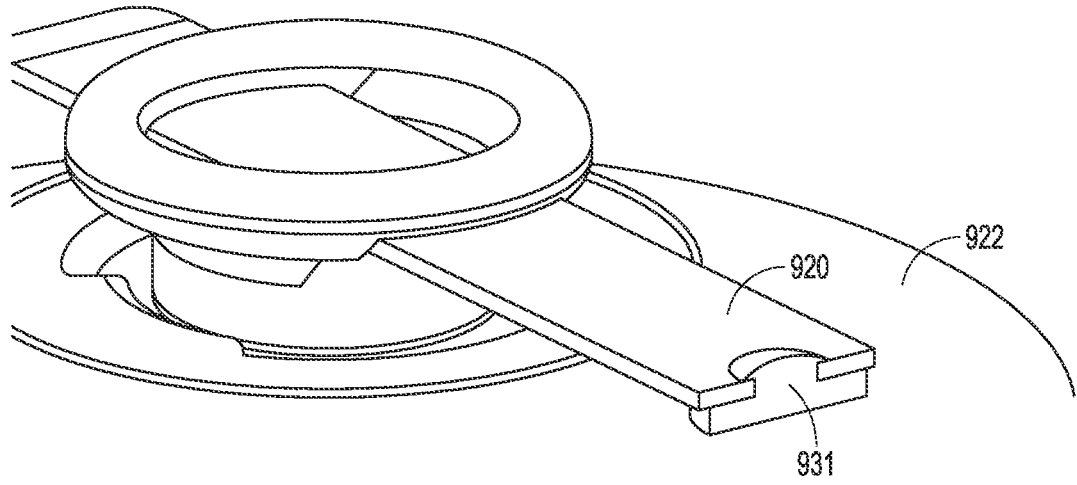
FIG. 9 illustrates, by way of example and not limitation, another embodiment for securing a coil assembly to an arm.

FIG. 9 illustrates, by way of example and not limitation, another embodiment for securing a coil assembly 922 to an arm 920. The end of arm 920 may include an aperture through which a stopper 931 (e.g., rubber stopper) may be inserted. The stopper may be removed to install or remove the coil assembly 922 off of the arm, but then can be inserted when the coil assembly 922 is on the arm 920.

Figure 10A:
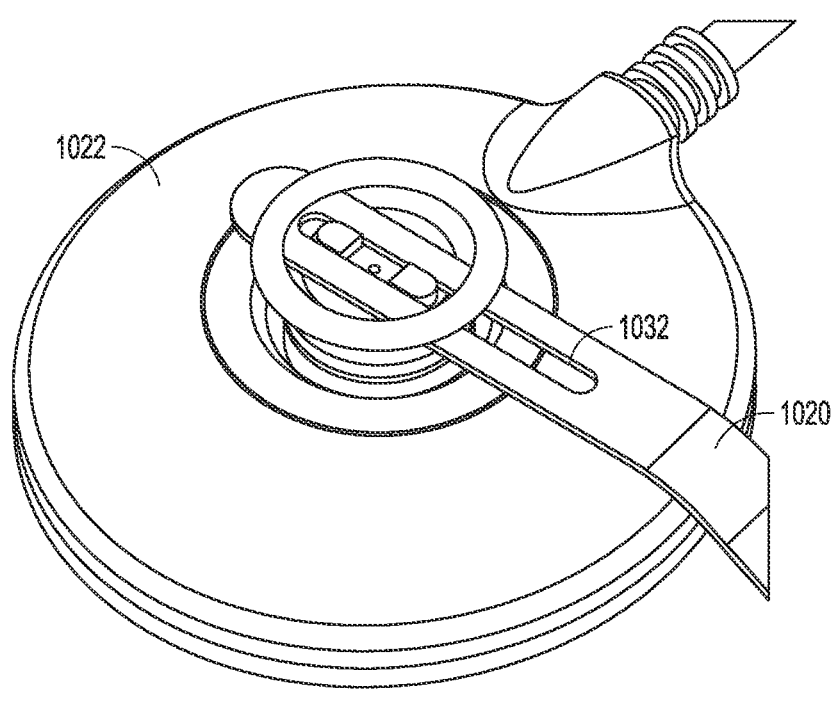
FIGS. 10A-10B illustrate, by way of example not limi-tation, another example of an attachment of a coil assembly to an arm using a slot within the arm and a washer that has diagonally-oriented alignment elements.
Figure 10B:
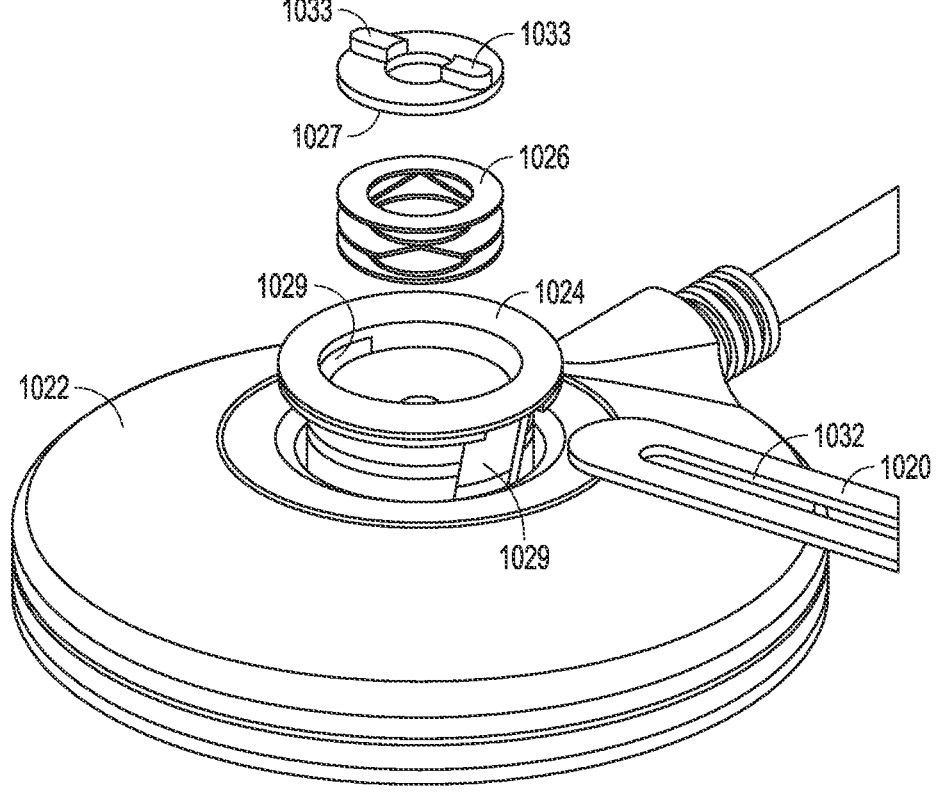

FIGS. 10A-10B illustrate, by way of example not limitation, another example of an attachment of a coil assembly 1022 to an arm 1020 using a slot 1032 within the arm 1020 and a washer 1027 that has alignment elements 1033 configured to be engaged within the slot 1032 of the arm 1020. The spring (e.g., wave spring) 1026 and then the washer 1027 are inserted into the connector portion 1024 of the coil housing, and arm 1020 may be inserted into the apertures 1029, allowing the alignment elements 1033 of the washer 1027 to engage the slot 1032 in the arm 1020.

Figure 11:
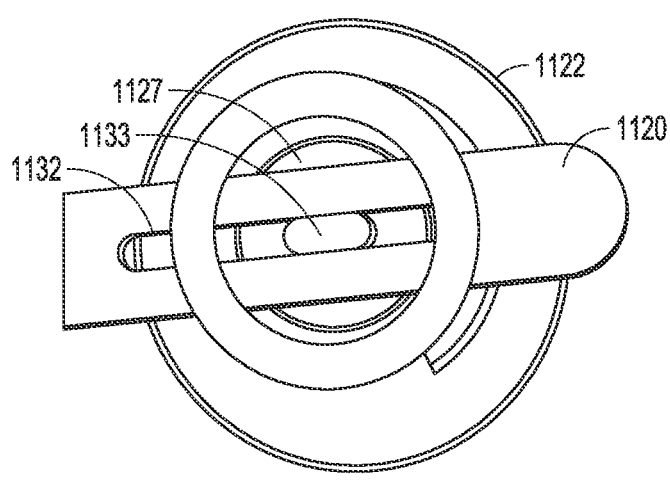
FIG. 11 illustrates, by way of example not limitation, another example of an attachment of a coil assembly to an arm using a slot with the arm and a washer with a single, centrally located alignment element.

FIG. 11 illustrates, by way of example not limitation, another example of an attachment of a coil assembly 1122 to an arm 1120 using a slot 1132 with the arm 1120 and a washer 1127 with a single, centrally located alignment element 1133 configured to be engaged with the slot 1132 with the arm 1120. A spring and the washer 1127 may be inserted into the connector portion of the coil housing, and then the arm 1120 may be inserted similar to the embodiment illustrated in FIG. 10B.

Figure 12A:
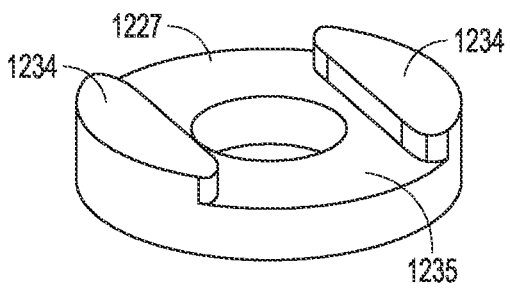
FIGS. 12A and 12B illustrate, by way of example and not limitation, another embodiment where the washer has a recessed portion between alignment elements for receiving the arm.
Figure 12B:
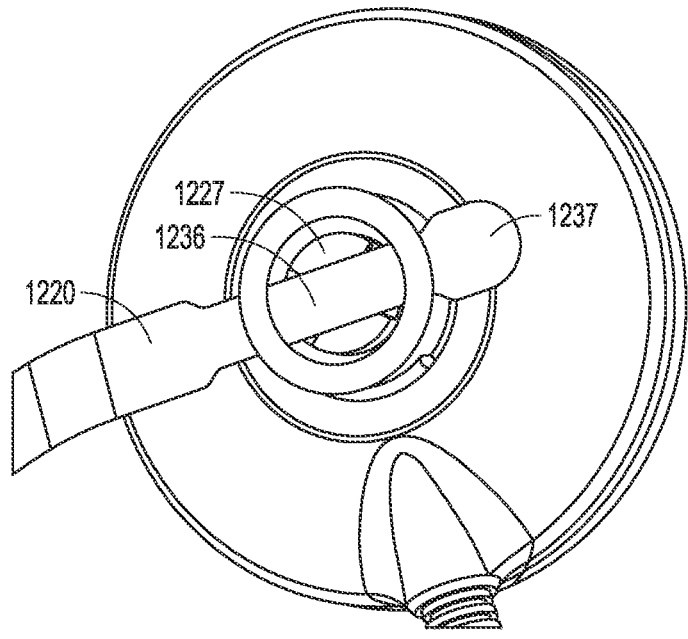

FIGS. 12A and 12B illustrate, by way of example and not limitation, another embodiment where the washer 1227 has a recessed portion 1235 between alignment elements 1234 for receiving the arm 1220. Rather than the slot 1032 in FIGS. 10A-10B, the arm may have a narrower portion 1236 to fit within the slot 1032 of the washer 1227. When the arm 1220 is inserted, the washer 1227 may be pressed in against the spring (not shown) to allow a wider tip 1237 of the arm to pass through the connector portion until the narrower portion 1236 of the arm is aligned with the slot 1032 of the washer 1227.

Figure 13:
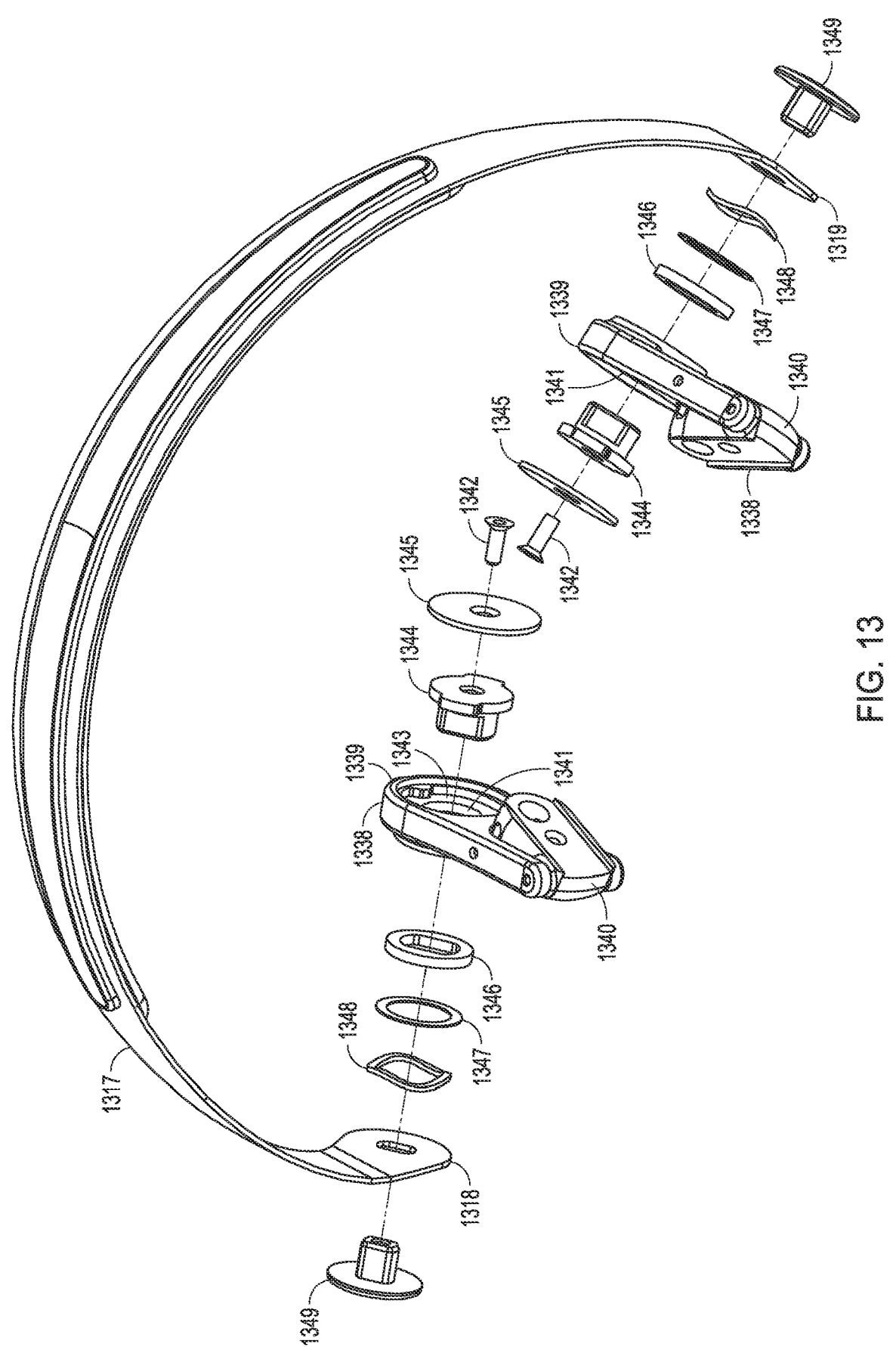
FIG. 13 illustrates, by way of example and not limitation, an exploded view for part of the headset.

FIG. 13 illustrates, by way of example and not limitation, an exploded view for part of the headset. The headset band 1317 is sized and is configured to be worn on a head of a patient. The headset band 1317 includes a first end 1318 and a second end 1319. When the headset band is worn on the head, the first end 1318 is on a first side of the head and the second end 1319 is on a second side of the head. The arms are rotatably connected to the headset using arm brackets 1338 (see, for example, FIG. 18 where the arms 1820 and 1821 are connected to the arm brackets 1838, which are connected to the headset 1817). The arm brackets 1338 are attached near the ends of the headset band 1317. The arm brackets 1338 include a first bracket end portion 1339 and a second bracket end portion 1340 and an aperture 1341 extending therethrough at the first bracket end portion 1339 for a fastener 1342 to extend through to connect to the headset band. The first bracket end portion 1339 includes a recess 1343 with the aperture 1341 extending through the recess. A bearing 1344 is configured to fit within the recess 1343. A feature in the recess engages with a feature in the bearing to limit rotational motion of the arm. The fastener 1342 may extend through a washer 1345 to connect the bearing 1344, the arm bracket 1338, a D-shaped washer 1346, a shim 1347 and a spring (e.g., wave spring) 1348 to an outer pivot 1349. The spring between the headset band and the first bracket end portion provides a clamping force between the D-shaped washer 1346 and the bearing 1344 that acts upon the arm bracket 1338 to provide some resistance to rotation to maintain the position of the arms once they are positioned by the user. However, the resistance is sufficiently small that the user can easily rotate the arms to properly position the coils. The outer pivot 1349 may have a threaded portion configured to extend through the D-shaped washer into the bearing 1344. The fastener 1342 is configured to engage threads in the threaded portion of the outer pivot.

Figure 14A:
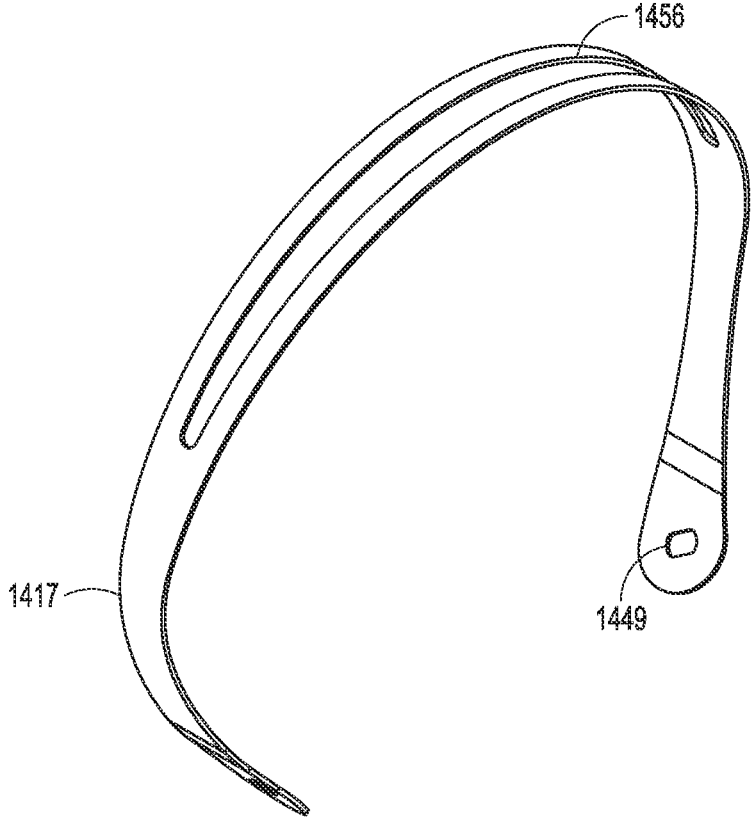
FIGS. 14A-14C illustrate, by way of example and not limitation, various views for an embodiment of the headset band.
Figure 14C:
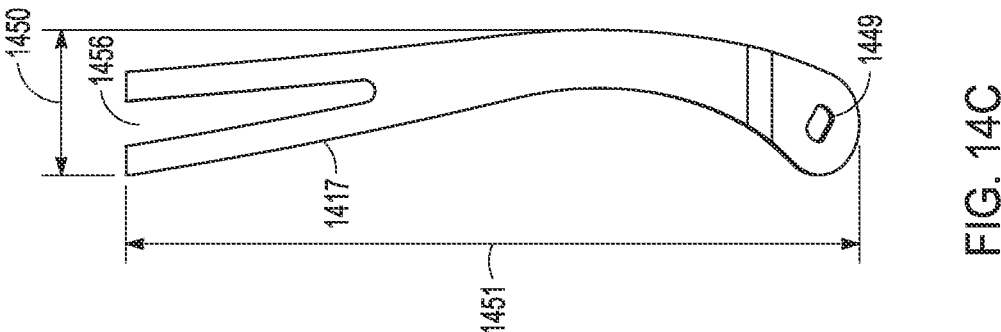
Figure 14B:
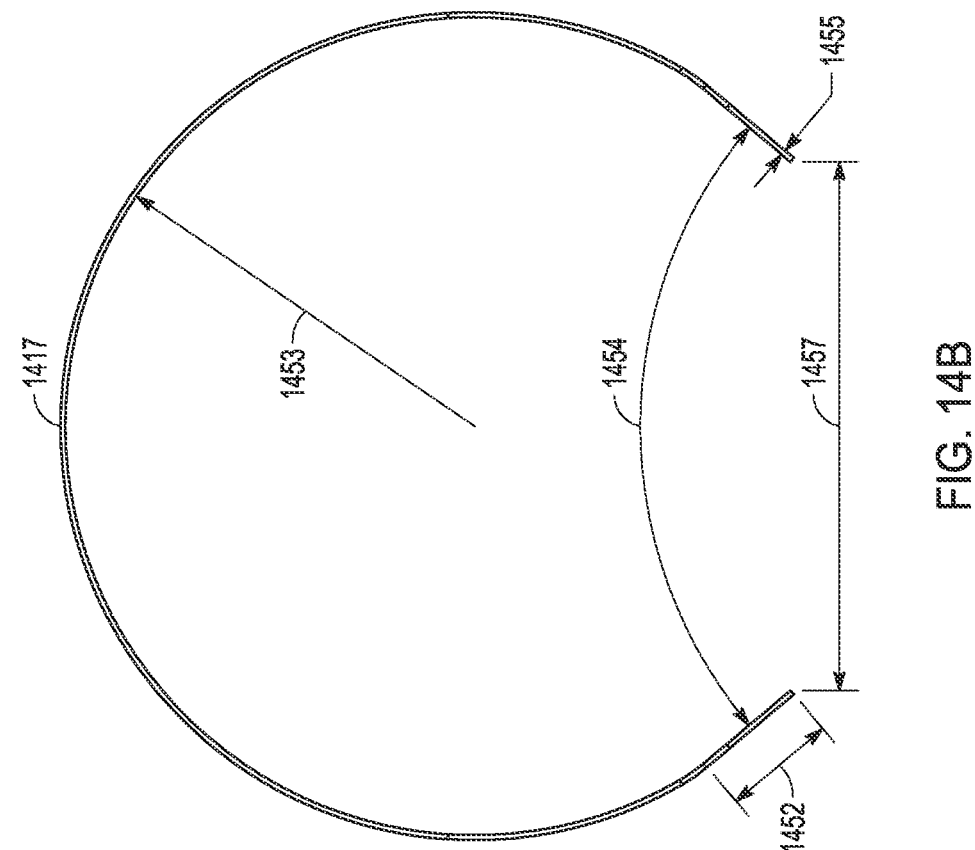
Figure 15A:
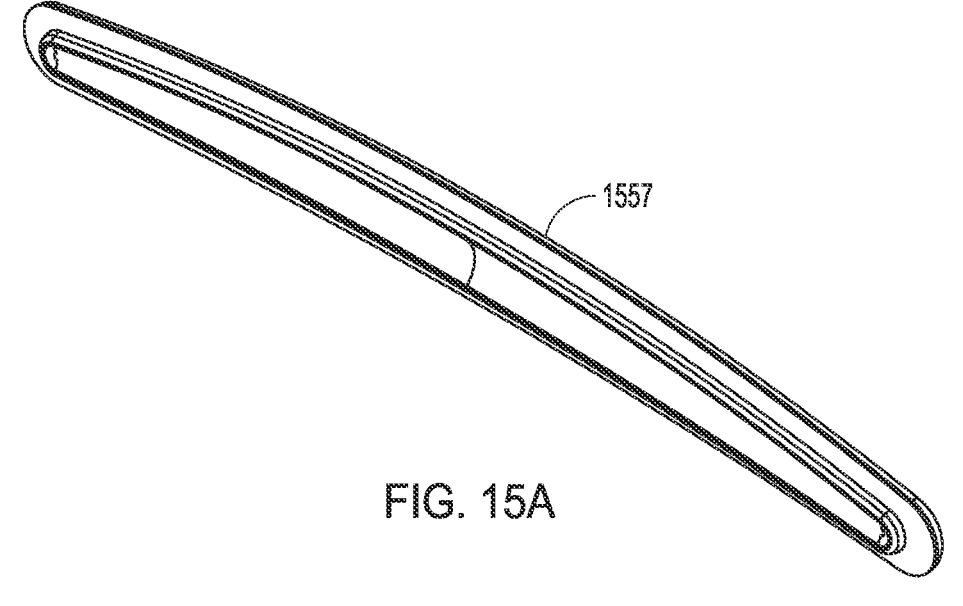
FIGS. 15A-15E illustrate, by way of example and not limitation, various views for an embodiment of a headset band pad.
Figure 15B:
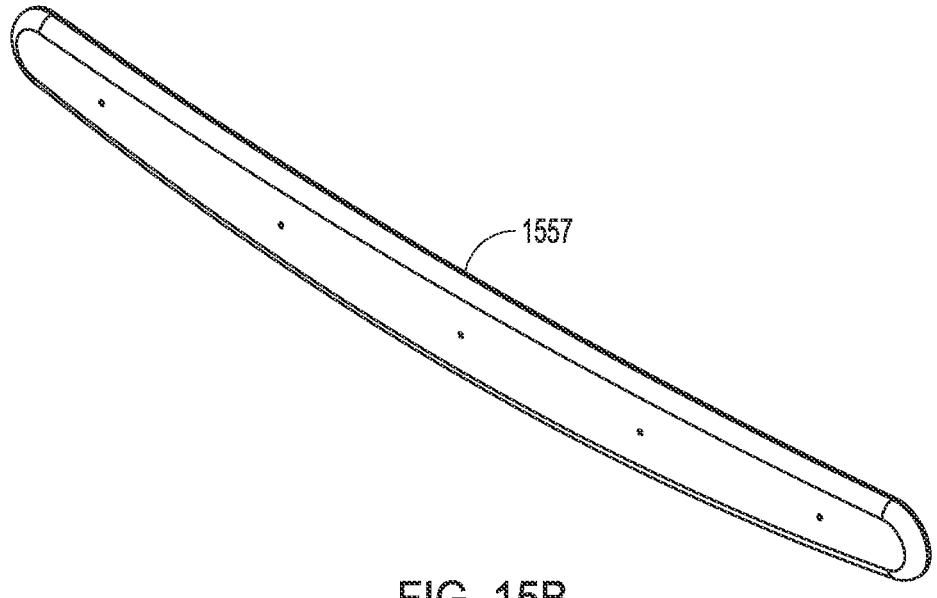
Figure 15C:
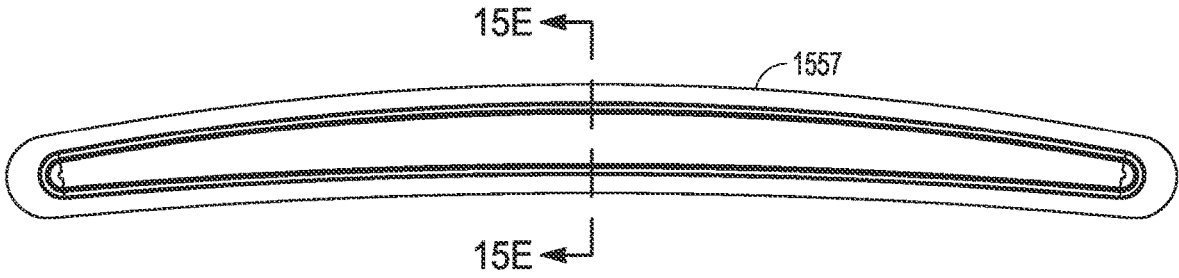
Figure 15D:
Figure 15E:
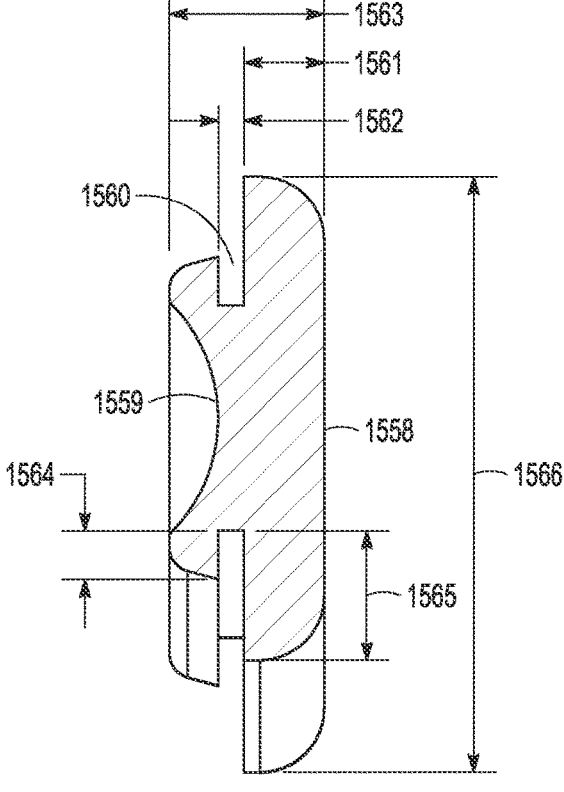

FIGS. 14A-14C illustrate, by way of example and not limitation, various views for an embodiment of the headset band 1417. Each end of the headset includes an elongated opening 1449 through which the threaded portion of the outer pivot (see FIG. 13, 1349) may extend. The opening may have a non-circular cross-sectional shape and the outside of the threaded portion may have a cooperating non-circular cross-sectional shape to prevent rotation between the pivot and the headset band. The headset band 1417 may have a width 1450 and height 1451 as illustrated in FIG. 14C. By way of example and not limitation, the height may be about 4.5 inches and the width may be about 9/10 of an inch. The ends may have flat portions for a length 1452, and an arching middle portion between the flat portions. By way of example and not limitation, the arching middle portion may have a radius 1453 of about 2.5 inches and the length 1452 of the flat portions may be about 7/10 of an inch, the angle 1454 between the flat portions may be about 80 degrees. The thickness of the headset band 1417 may be about 3/100 of an inch. The headset band has an ability to retain shape, and may be fabricated from stainless steel, by way of example and not limitation. The headset band may be flexed out at the ends when placing on the head and has an ability to retain shape to apply pressure toward the head when worn on the head. The headset band also may be capable of some degree of twisting motion. The headset band may include a slot 1456 for use to receive a headset band pad (see pad in FIGS. 15A-15E). The distance 1457 between the ends of the headset band may be about 3 to 3.5 inches.

FIGS. 15A-15E illustrate, by way of example and not limitation, various views for an embodiment of a headset band pad 1557. With reference to the cross-section view illustrated in FIG. 15E, the headset band pad may include a top portion 1558 and a bottom portion 1559. A gap 1560 between the bottom portion 1559 and top portion 1560 receives the slot edges of the headset band 1417. The pad 1557 is flexible, such that the bottom portion 1559 may be flexed to fit within the slot of the headset band pad but rigid enough to be retained. The bottom portion 1559 may provide padding between the head and the headset band for comfort and to prevent unintentional movement of the headset band. The thickness 1561 of the top portion of the pad may be about 1/10 of an inch, the thickness 1562 of the gap between the top and bottom portions may be about 3/100 of an inch, and the overall thickness of the headset band pad 1563 may be about 19/100 of an inch. The feet of the bottom portion may have a thickness 1564 of about 6/100 of an inch. The top portion 1558 may have an overhang 1565 of about 16/100 of an inch. The pad width 1566 may be about 7/10 to 8/10 of an inch. Some embodiments fabricate the pad from food grade silicone.

Figure 16A:
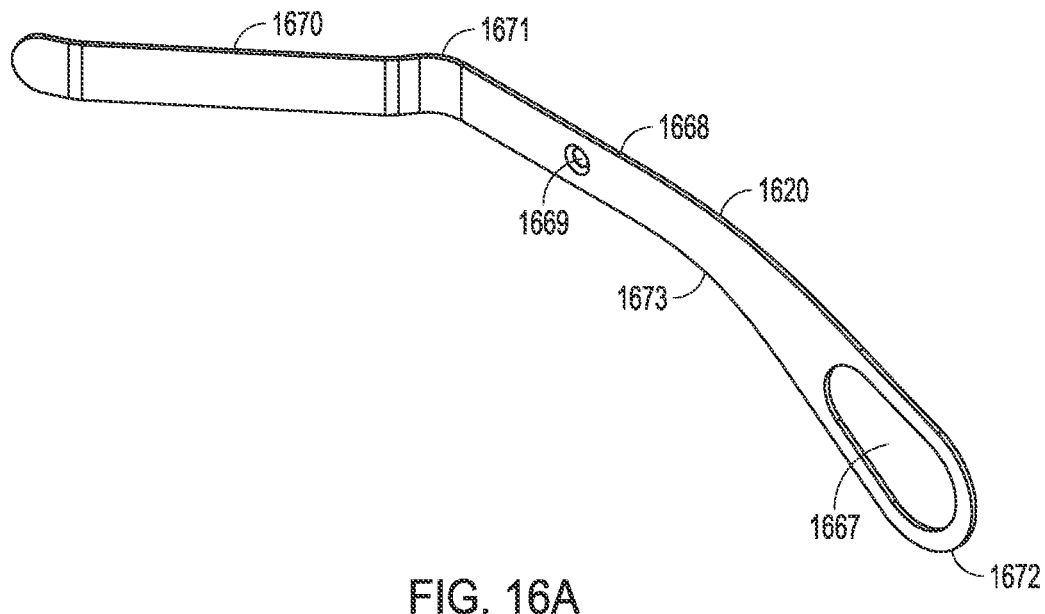
FIGS. 16A-16C illustrate, by way of example and not limitation, various views for the arms.
Figure 16B:
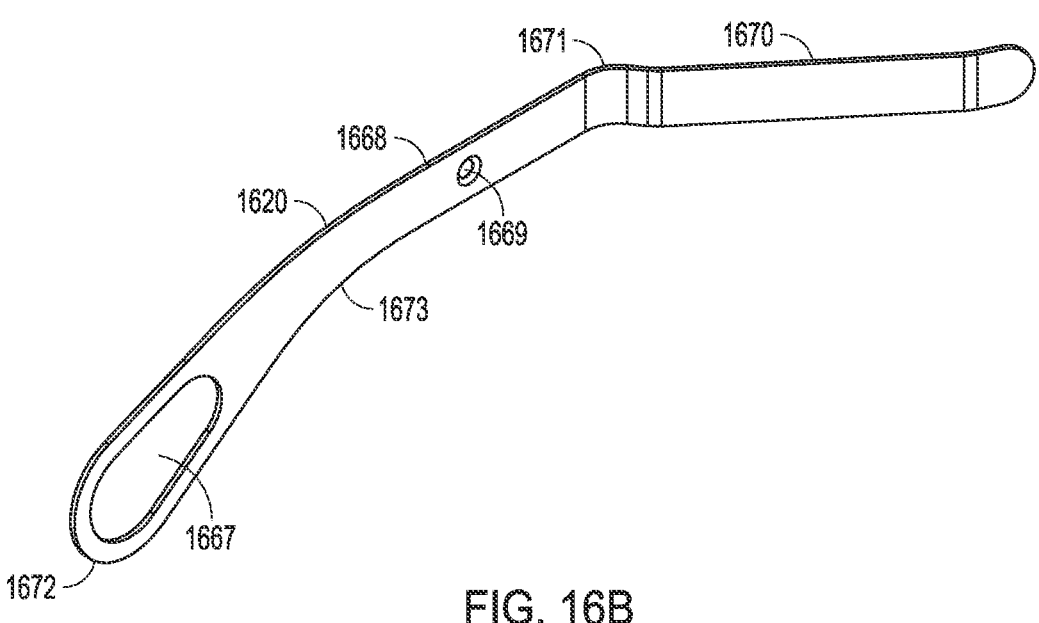
Figures 16C, 17:
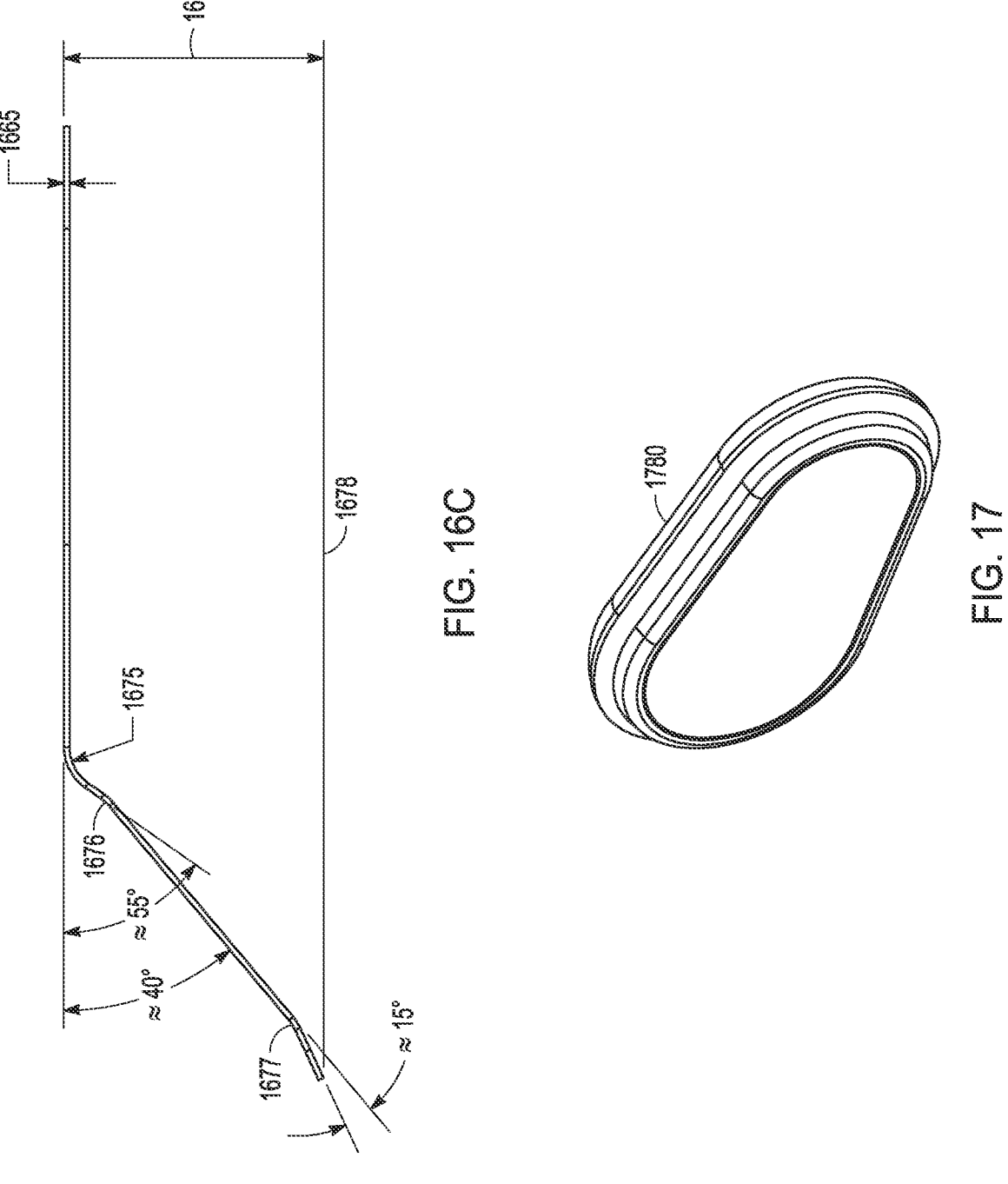
FIG. 17 illustrates, by way of example and not limitation, a temple pad, which may be inserted into the aperture in the arms.

FIGS. 16A-16C illustrate, by way of example and not limitation, various views for the arms (e.g., first arm 1620 and second arm 1621). Each arm includes a temple pad aperture 1667 for use to receive a temple pad. Each arm includes a connection portion 1668, with an aperture 1669 therein, to make a connection to the headset band, and further includes a coil portion 1670 on which the coil assembly is attached. Each arm has a bend 1671 between the coil portion 1670 and the connection portion 1668. Each arm may have a temple portion 1672, and a downward bend 1673 between the temple portion 1672 and the connection portion 1668. Each of the arms curve inward toward the head when worn on the head. The thickness 1665 of the arm may be about 3/100 of an inch. The bend 1671 may be more than one bend, such as a first bend 1675 in a first direction with a radius of about 1/4 inch to provide about a 55-degree angle with respect to the connection portion 1668, and a second bend 1676 in a second direction to provide about a 40-degree angle with respect to the connection portion 1668. The end of the arm may include a bend 1677 such as to provide about a 15-degree angle. The second bend 1676 may provide a travel stop for coil assembly movement similar to the bend 1677 (see also FIG. 8, bent end portion 830). The total length 1678 of the arm may be about 5½ to 6 inches, and the height 1679 may be about 1.4 inches. The arms may be fabricated from stainless steel, and may be capable of flexing while still maintaining an initial shape.

FIG. 17 illustrates, by way of example and not limitation, a temple pad 1780, which may be inserted into the aperture 1667 in the arms. The temple pad 1780 may have a profile similar with similar thicknesses to the headset band pad 1557 (see FIGS. 15A-15E, with a width of about 7/10 to 8/10 of an inch. Some embodiments fabricate the temple pad from food grade silicone.

Figure 18:
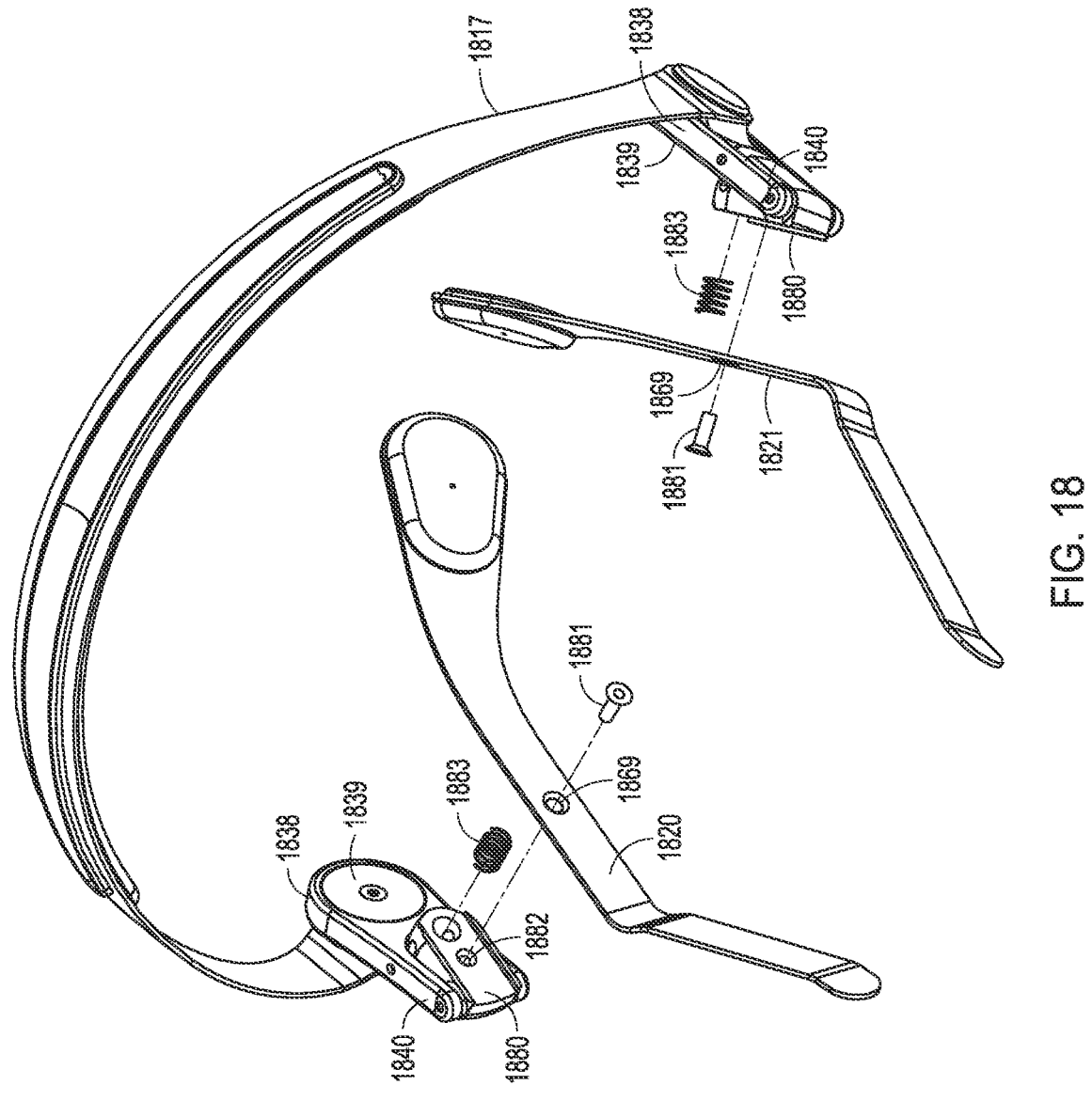
FIG. 18 illustrates, by way of example and not limitation, a partially exploded view for attaching arms to the headset band.
Figure 19:
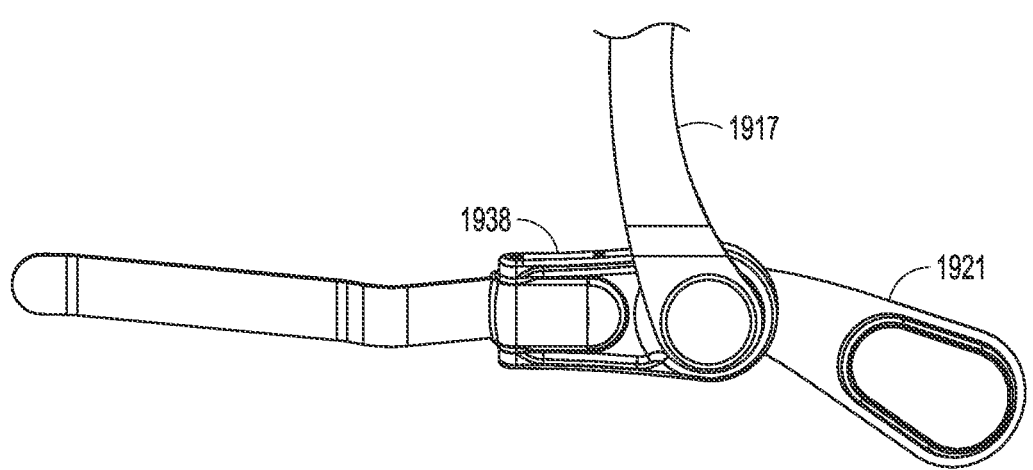
FIG. 19 illustrates, by way of example and not limitation, an assembled arm bracket attached to an arm and the headset band.
Figures 20A, 20B, 20C, 20D:
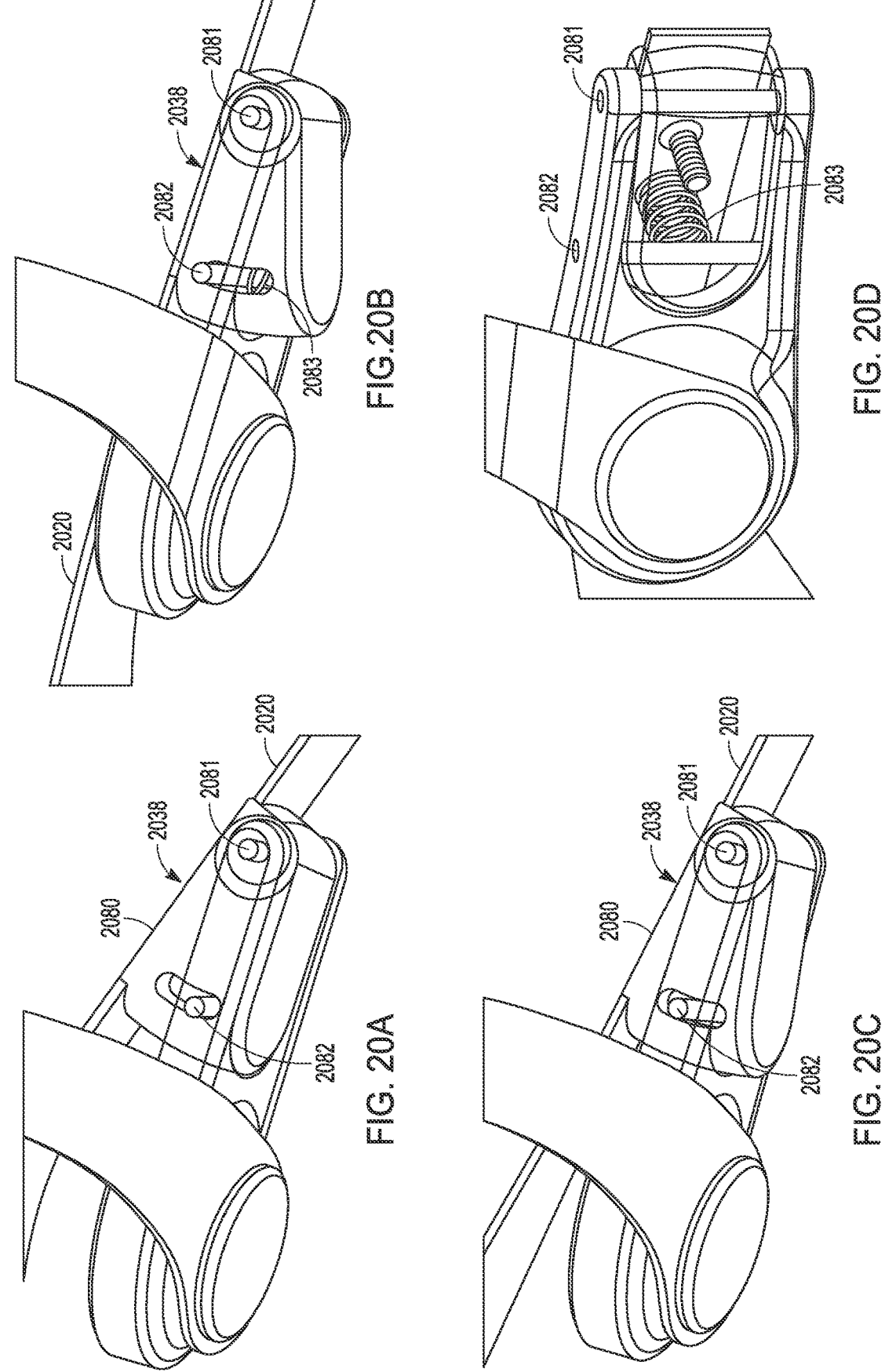
FIGS. 20A-20D illustrate, by way of example and not limitation, the limited pivoting motion of the pivot portion of the arm bracket and thus the limited motion of the attached arm.

FIG. 18 illustrates, by way of example and not limitation, a partially exploded view for attaching arms to the headset band. The arm brackets 1838 are shown attached to the headset band 1817 (see FIG. 13). The arms 1820 and 1821 are rotatably connected to the headset band 1817 using the arm brackets 1838. The arm brackets 1338 include a first bracket end portion 1839 and a second bracket end portion 1840. The second bracket end portion 1840 includes a pivot portion 1880 configured to pivot, with limited motion about a pin. A fastener 1881 may be inserted through the aperture 1869 in the connection portion 1868 of the arm and into an aperture 1882 in the pivot portion 1880 to connect the arm to the pivot portion 1880 of the arm bracket 1838. A spring 1883 may fit within a spring aperture 1884 to provide a slight force against the arm to prevent undesired motion (e.g., "rattling") of the arm when the headset is not being worn. FIG. 19 illustrates, by way of example and not limitation, an assembled arm bracket 1938 attached to an arm 1921 and the headset band 1917.

FIGS. 20A-20D illustrate, by way of example and not limitation, the limited pivoting motion of the pivot portion 2080 of the arm bracket 2038 and thus the limited motion of the attached arm 2020. The arm bracket includes a pivot pin 2081 about which the pivoting portion 2080 moves, and a stop pin 2082 to limit the pivoting motion. Also shown is the spring 2083.

FIG. 21 illustrates, by way of example and not limitation, a partially-exploded view of the arm bracket 2138 with the pivot pin 2181 and stop pin 2182 being inserted. The arm bracket 2138 includes a bracket frame 2184 and a pivot portion 2180. The bracket frame 2184 includes first bracket end portion 2139, which has a recess 2143 with an aperture 2141 extending through the recess. A bearing is configured to fit within the recess 2143, and a feature 2185 in the recess engages with a feature in the bearing to limit rotational motion of the arm. Bracket frame arms 2186 include pin apertures for the pivot pin and stop pin.

FIG. 22A-22B illustrate, by way of example and not limitation, front and rear perspective views of the bracket frame 2284. The bracket frame 2284 includes a recess 2243, a feature 2285 in the recess 2243 to engage a bearing feature, and bracket frame arms 2286 with pin apertures.

Figures 23A, 23B:
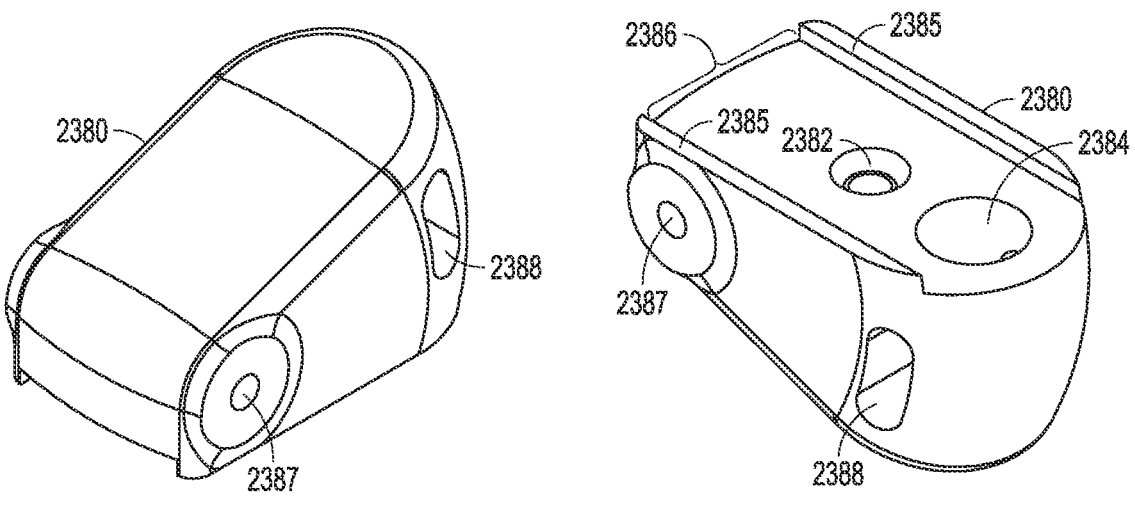
FIGS. 23A-23B illustrate, by way of example and not limitation, front and rear perspective views of the pivot portion.

FIGS. 23A-23B illustrate, by way of example and not limitation, front and rear perspective views of the pivot portion 2380. The pivot portion includes a pivot pin aperture 2387 to receive the pivot pin, and further includes a slotted stop pin aperture 2388 to receive the stop pin. The fastener aperture 2382, which may be threaded, and the spring aperture 2384 are also shown. As seen in FIG. 23B, the pivot portion 2380 has side edges 2385 that form a slot 2386 to receive an arm when the arm is fastened to the pivot portion 2380. This slot feature constrains the arm from rotation with respect to the pivot portion.

Figure 24:
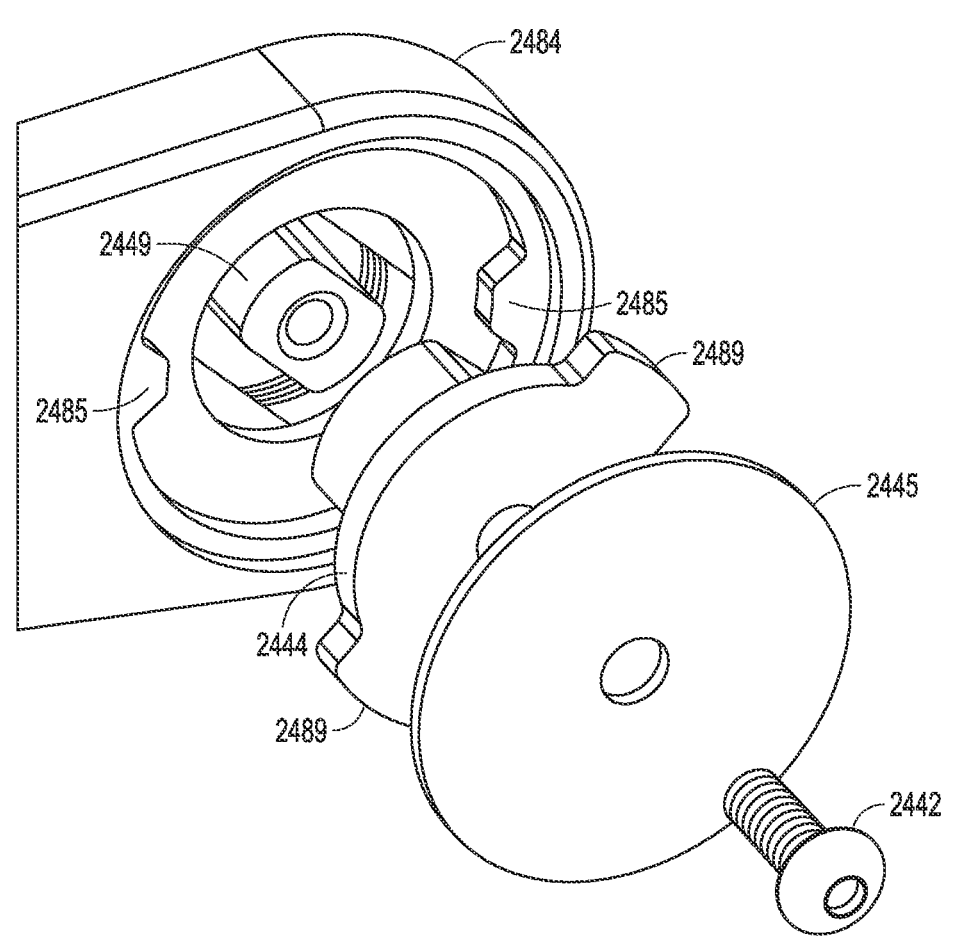
FIG. 24 illustrates, by way of example and not limitation, a partial exploded view of the fastener being inserted through the washer and the bearing 2444 and into the threaded portion of the outer pivot.
Figure 25:
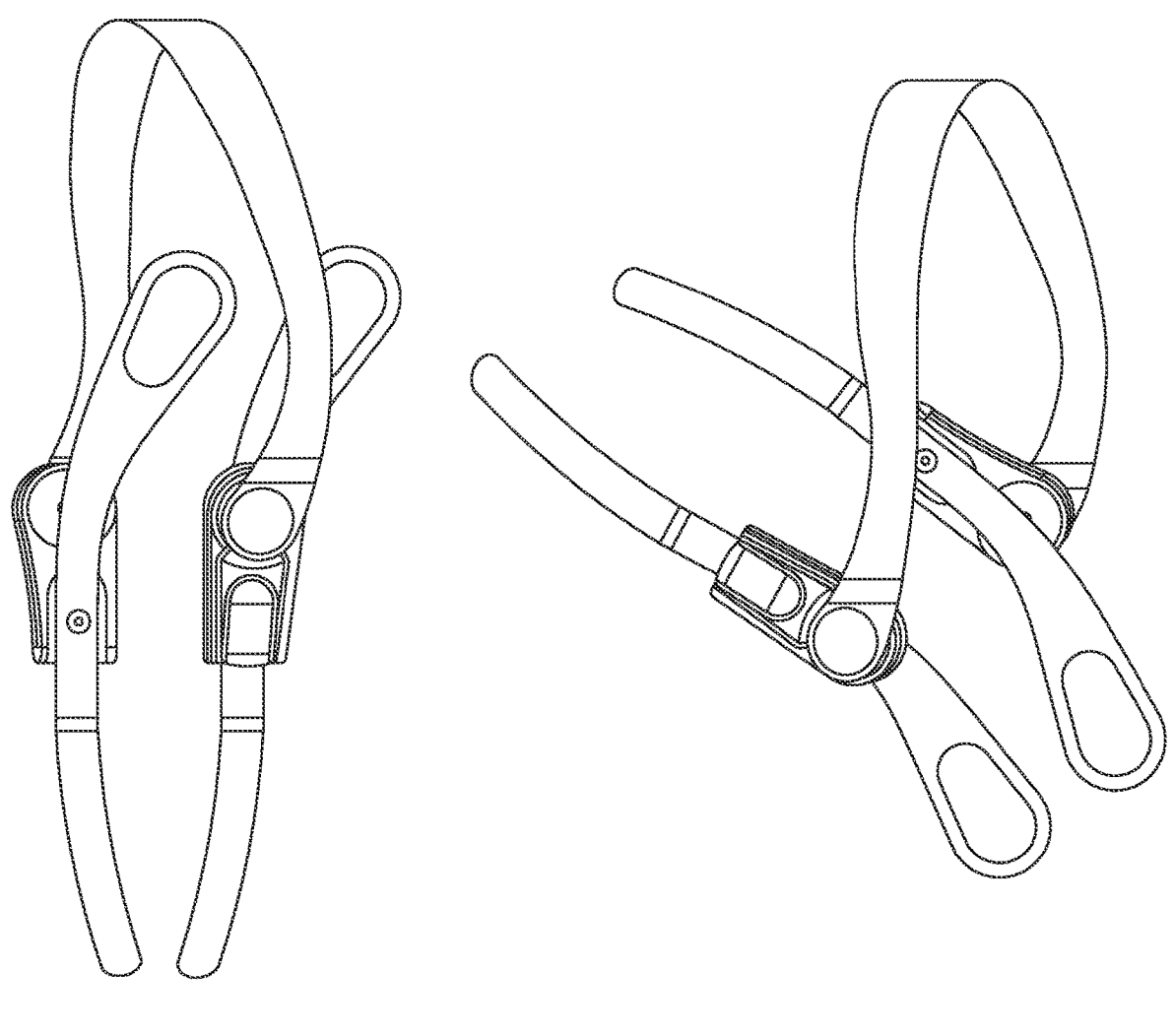
FIGS. 25A-25B illustrate, by way of example and not limitation, limits in arm motion.

FIG. 24 illustrates, by way of example and not limitation, a partial exploded view of the fastener 2442 being inserted through the washer 2445 and the bearing 2444 and into the threaded portion of the outer pivot 2449. This figure further illustrates the features 2485 in the recess and the bearing features 2489 that engage each other to limit rotational motion. The threaded portion of the outer pivot 2449 functions as key into an aperture of the bearing 2444 and an aperture of the headset band, thus fixing the bearing with respect to the headset band. The bracket frame 2484 is able to rotate, with limited rotational motion, with respect to the bearing. 2444. FIGS. 25A-25B illustrate the extents of the limited motion of the arms because of the design of the bracket frame and the bearing.

FIG. 26 illustrates the D-shaped washer 2646 (see FIG. 13 1346), FIG. 27 illustrates the bearing 2744 (see FIG. 13 1344), FIG. 28 illustrates the washer 2845 (see FIG. 13 1345), and FIGS. 29A-29B illustrate the outer pivot 2949 (see FIG. 13 1349). The threaded portion of the outer pivot is not cylindrical but functions as a key when inserted into the D-shaped aperture of the bearing. The D-shaped washer is configured to allow the threaded portion to extend through the washer to the bearing.

Figure 30:
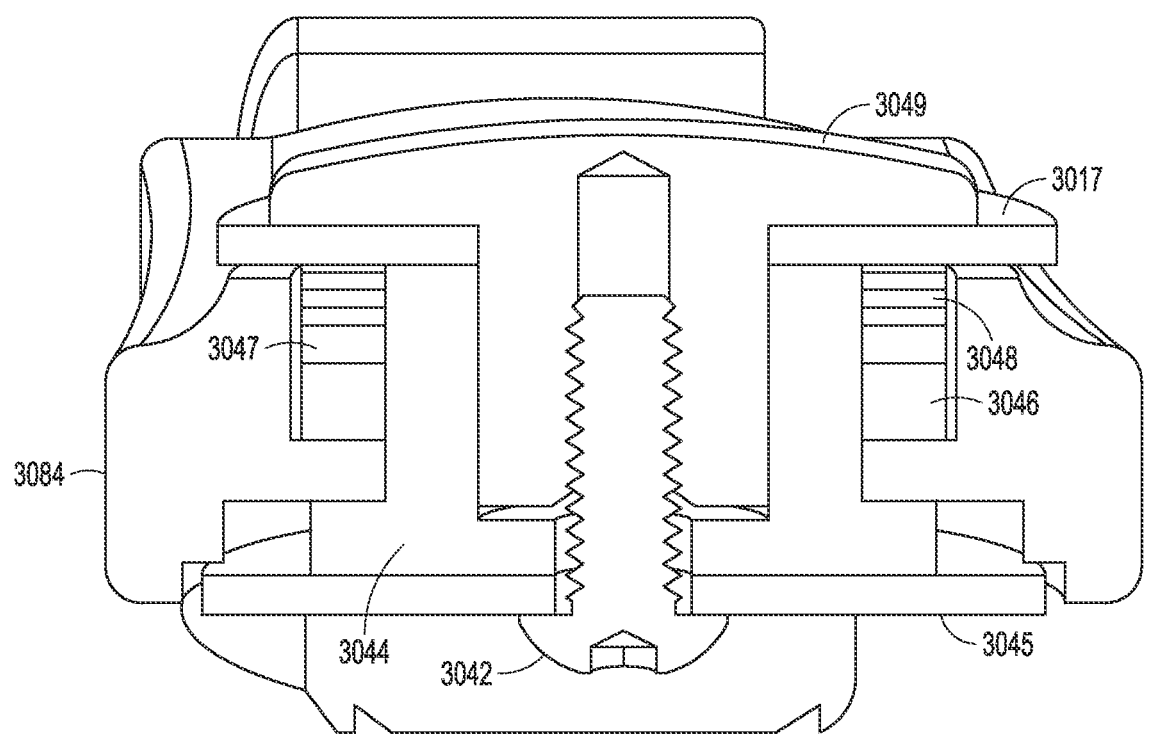
FIG. 30 illustrates, by way of example and not limitation, a cross section of a portion of the assembled arm bracket.

FIG. 30 illustrates, by way of example and not limitation, a cross section of a portion of the assembled arm bracket.

The figure illustrated the fastener 3042 extending through the washer 3045 and the bearing 3044 into the threaded portion of the outer pivot 3049. The threaded portion of the outer pivot 3049 extends through a wave spring 3048, a shim 3047, a D-shaped washer 3046 into the aperture of the bearing. Thus, the threaded portion of the outer pivot 3049 functions as a key within an aperture of the headset band 3017 and the bearing 3044 to prevent rotational motion while still allowing axial motion. The bracket frame 3084 of the arm bracket has limited motion about the bearing. The spring (e.g., wave spring 3048) provides a clamping force between the D-shaped washer 3046 and the bearing 3044, which acts upon the bracket frame 3084. This provides some resistance to rotation to maintain the position of the arms once they are positioned by the user. However, the resistance is sufficiently small that the user can easily rotate the arms to properly position the coils.

Figure 31:
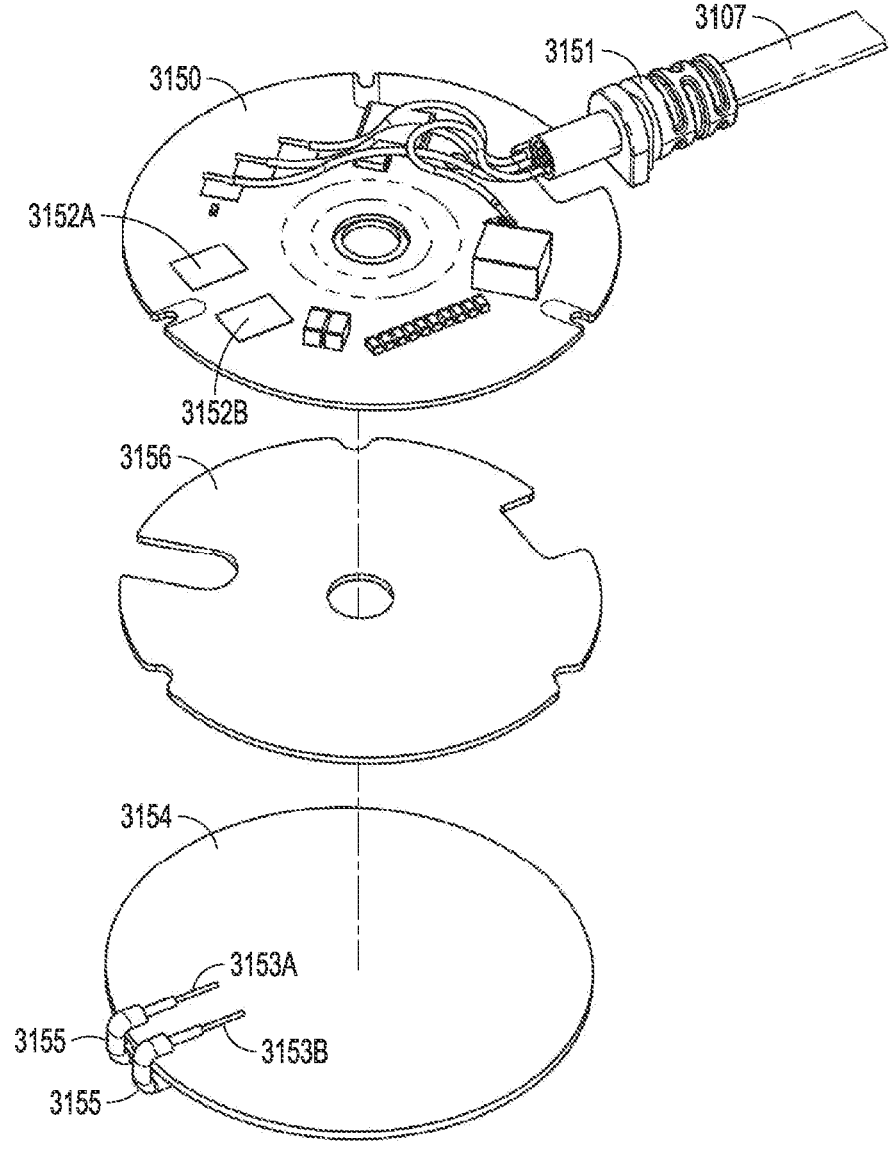
FIG. 31 illustrates, by way of example and not limitation, some components of a soldered subassembly for a coil assembly.

FIG. 31 illustrates, by way of example and not limitation, some components of a soldered subassembly for a coil assembly. As illustrated in the figure, a printed circuit board assembly (PCBA) 3150 is electrically connected to a cable 3107, such as cable 507A or 507B in FIG. 5. A strain relief 3151 for the cable is also illustrated. The PCBA includes solder pads 3152A and 3152B for use to make an electrical connection to the ends 3153A and 3153B of the headset coil 3154. Silicone tubing 3155 may be provided around the ends 3153A and 3153B. A gasket 3156 may be positioned between the PCBA 3150 and the coil 3154.

Figure 32:
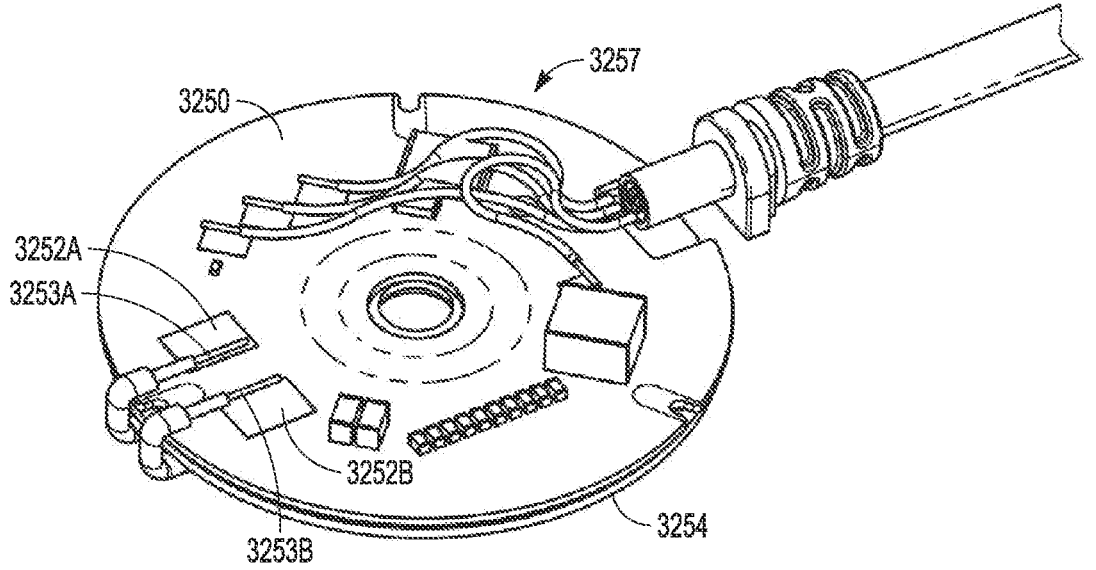
FIG. 32 illustrates the components illustrated in FIG. 31 assembled into a completed soldered subassembly.

FIG. 32 illustrates the components illustrated in FIG. 31 assembled into a completed soldered subassembly 3257. The ends 3253A and 3253B of the headset coil 3254 are soldered to the solder pads 3252A and 3252B on the PCBA 3250.

Figure 33:
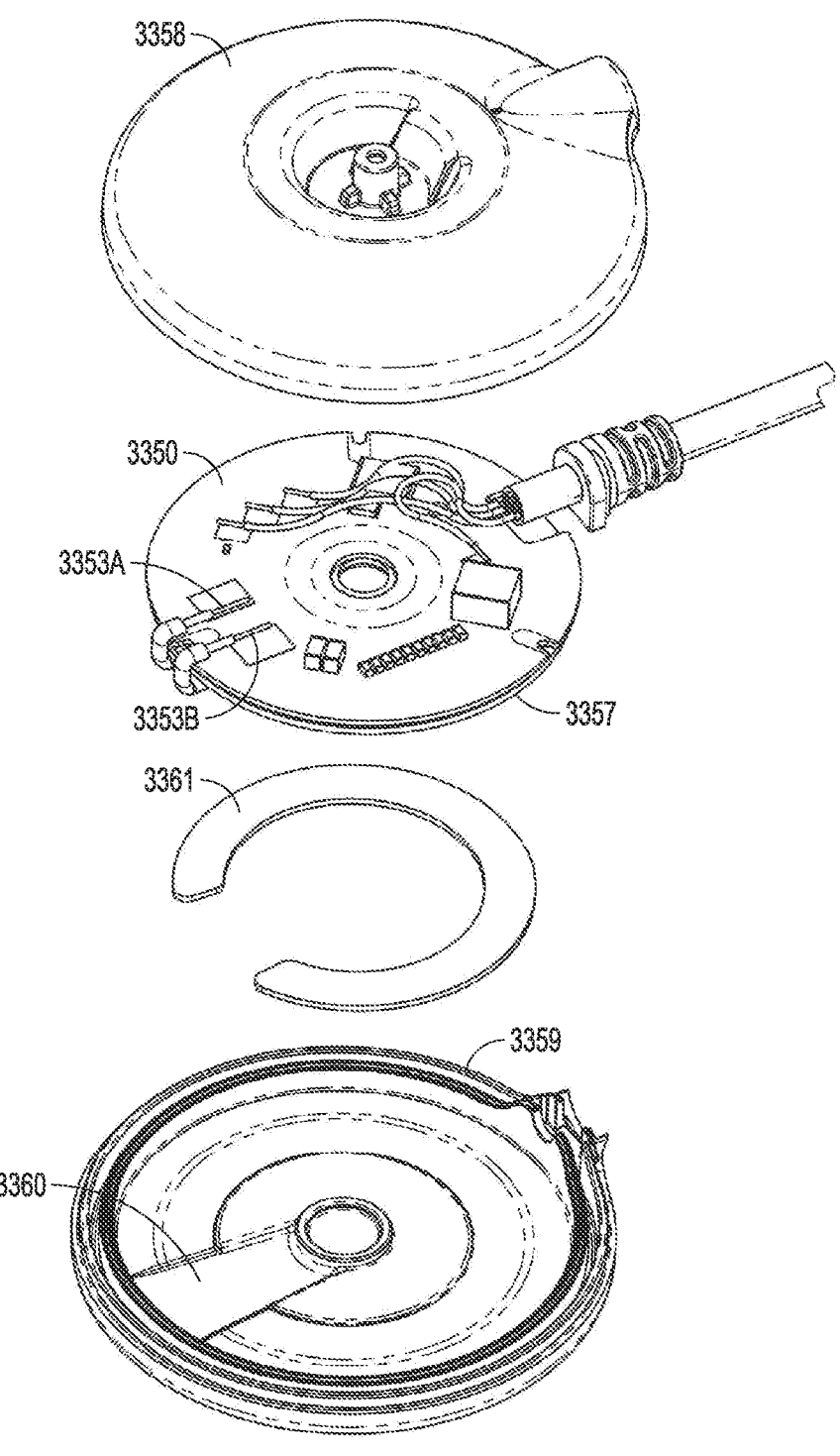
FIG. 33 illustrates, by way of example and not limitation, some components of a welded coil assembly.
Figure 34:
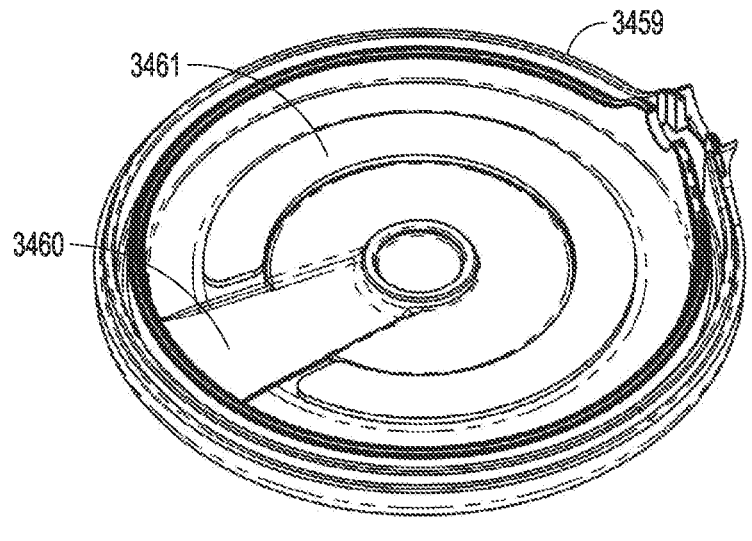
FIG. 34 illustrates placement of the gasket in the inner coil housing, with the ends of the gasket near the coil lead pocket.

FIG. 33 illustrates, by way of example and not limitation, some components of a welded coil assembly. The completed soldered subassembly 3357 may be positioned between an outer coil housing 3358 and an inner coil housing 3359. The inner coil housing 3359 includes a coil lead pocket 3360 in which coil leads may extend to the ends 3353A and 3353B of the headset coil. A gasket 3361 may be positioned between the soldered subassembly 3357 with the PCBA 3350 and the inner coil housing 3359. The gasket 3361 may have an arcuate shape forming an opening that corresponds to the coil lead pocket 3360. FIG. 34 illustrates placement of the gasket 3461 in the inner coil housing 3461, with the ends of the gasket 3461 near the coil lead pocket 3460.

Figure 35:
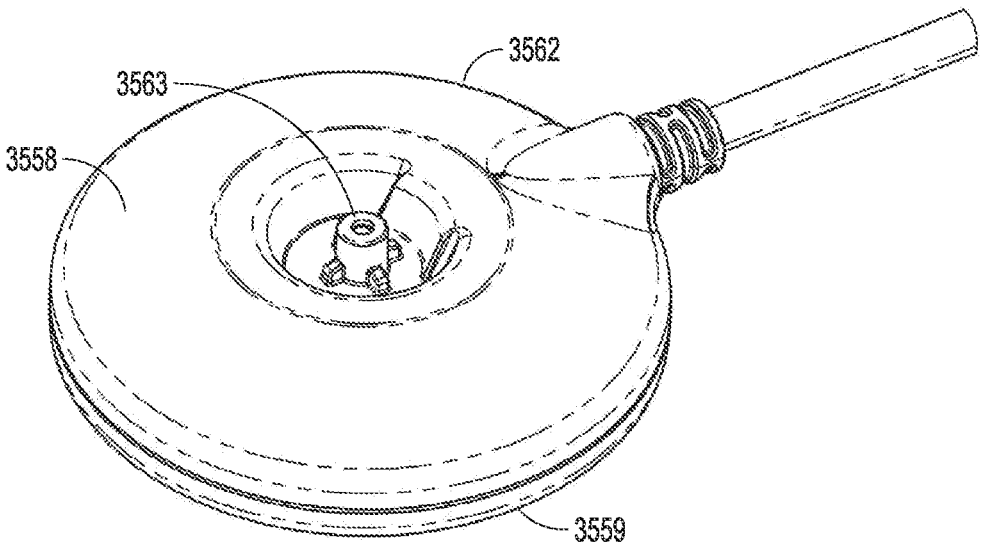
FIG. 35 illustrates the components of FIG. 33 assembled into a completed welded coil assembly.

FIG. 35 illustrates the components of FIG. 33 assembled into a completed welded coil assembly 3562. The outer coil housing 3358 may be bonded to the inner coil housing 3359. Ultrasonic welding may be used bond the outer coil housing 3358 to the inner coil housing 3359. The ultrasonic welds may provide a single enclosure that also provides a water penetration barrier as well as a safety barrier to higher voltage The ultrasonic welds allow smaller headset coil enclosures to be fabricated. The thickness of the sealed coil enclosures satisfies product safety requirements such as the creepage and clearance distance of the PCBA to the outside world. Additional creepage distance across a shorter distance is provided by features of the strain relief for the cable and the tongue and groove construction of the strain relief to the coil housing (see, for example, the exploded view of FIG. 33). The top of the outer coil housing 3358 may have a threaded aperture 3563 for receiving a threaded fastener (e.g., screw).

Figure 36:
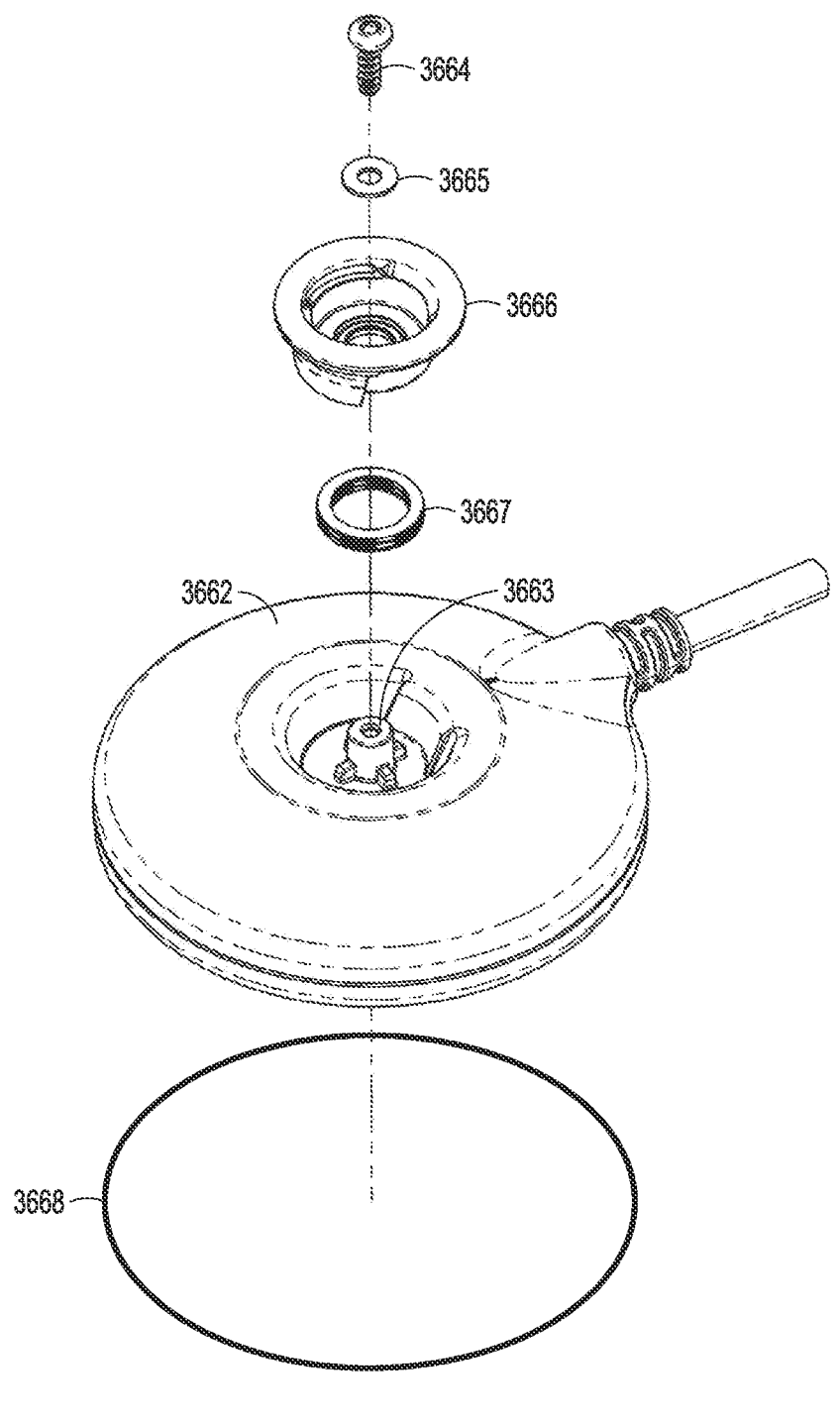
FIG. 36 illustrates, by way of example and not limitation, some components of completed coil assembly.

FIG. 36 illustrates, by way of example and not limitation, some components of completed coil assembly. A fastener 3664 may be fed through a washer 3665, a headset housing pivot 3666 (previously referred to as a connection portion of the housing (e.g., FIG. 7 at 725)), a spring 3667 (e.g., wave spring), and into the threaded aperture 3663 to connect the headset housing pivot 3666 to the welded coil assembly 3662. A housing pad 3668 may be attached to the bottom of the welded coil assembly 3662, where the assembly will contact the head.

Figure 37:
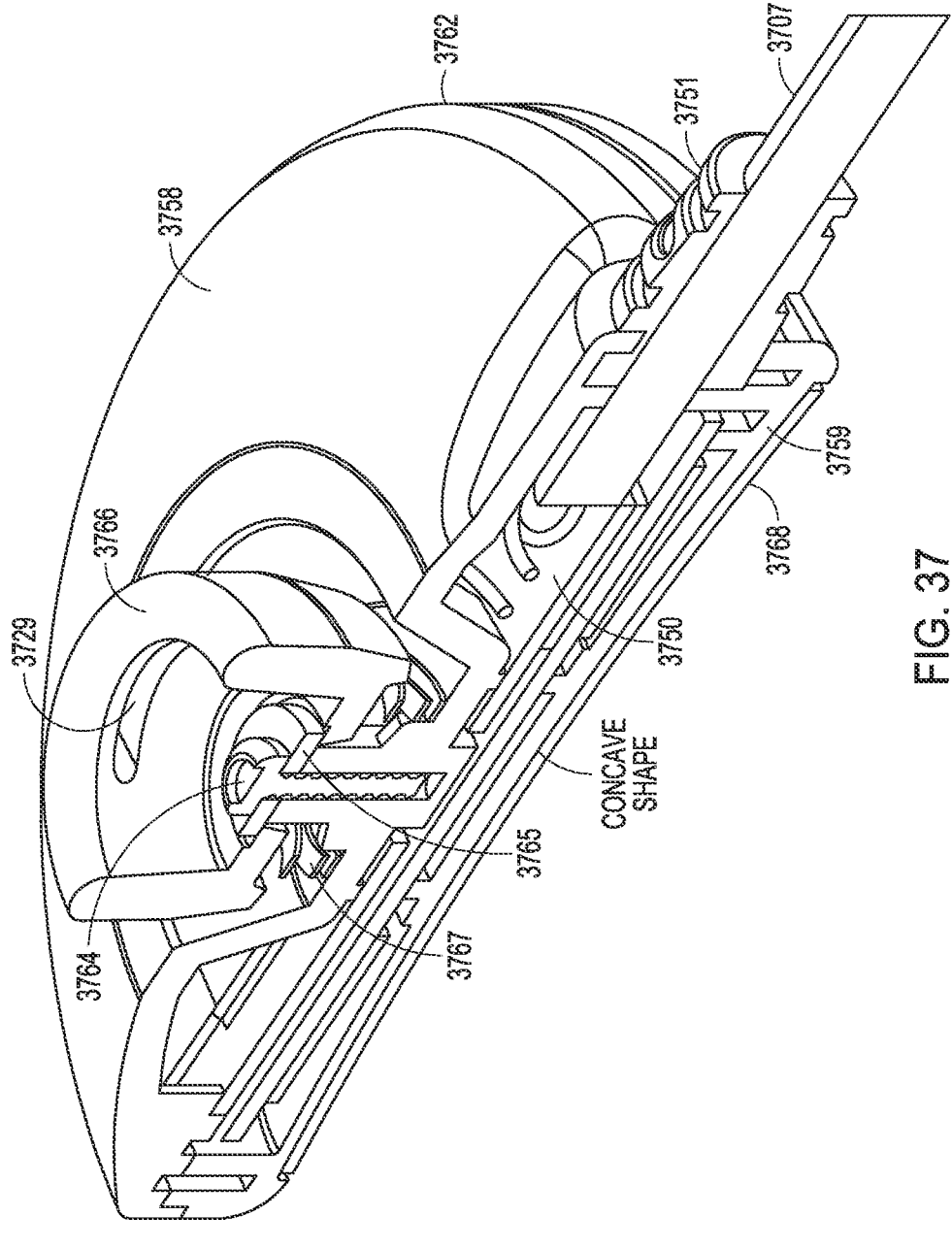
FIG. 37 illustrates a cut-away view of the completed coil assembly.

FIG. 37 illustrates a cut-away view of the completed coil assembly. The cable 3707 feeds into the welded coil assembly 3762, and a strain relief 3751 surrounds the cable 3707 and is attached to the welded coil assembly 3762. The headset housing pivot 3766 is fastened to the outer coil housing 3758. An aperture or slot 3729 is shown, through which an arm of the headset may be fed. The fastener 3764, washer 3765, spring 3767, PCBA 3750, inner coil housing 3759 and housing pad 3768 are also illustrated. The bottom surface of the inner coil housing 3759 may have a concave shape as illustrated in this cut-away view. The concave shape faces toward the head when the coil assembly contacts the head. The concave shape assists with coil alignment with the implantable medical device (e.g., see FIG. 1, 100, FIG. 3, 300, and FIGS. 4A-4B 400). The implantable medical device may provide a slight bulge and the concave shape tends to cause the coil assembly to center over the implantable medical device. Some embodiments may provide a simple concave shape as illustrated. Other embodiments may design the bottom surface with contours to closely match the shape of the implantable device to assist the user in properly aligning the coil assembly with the implantable medical device.

Figure 38A:
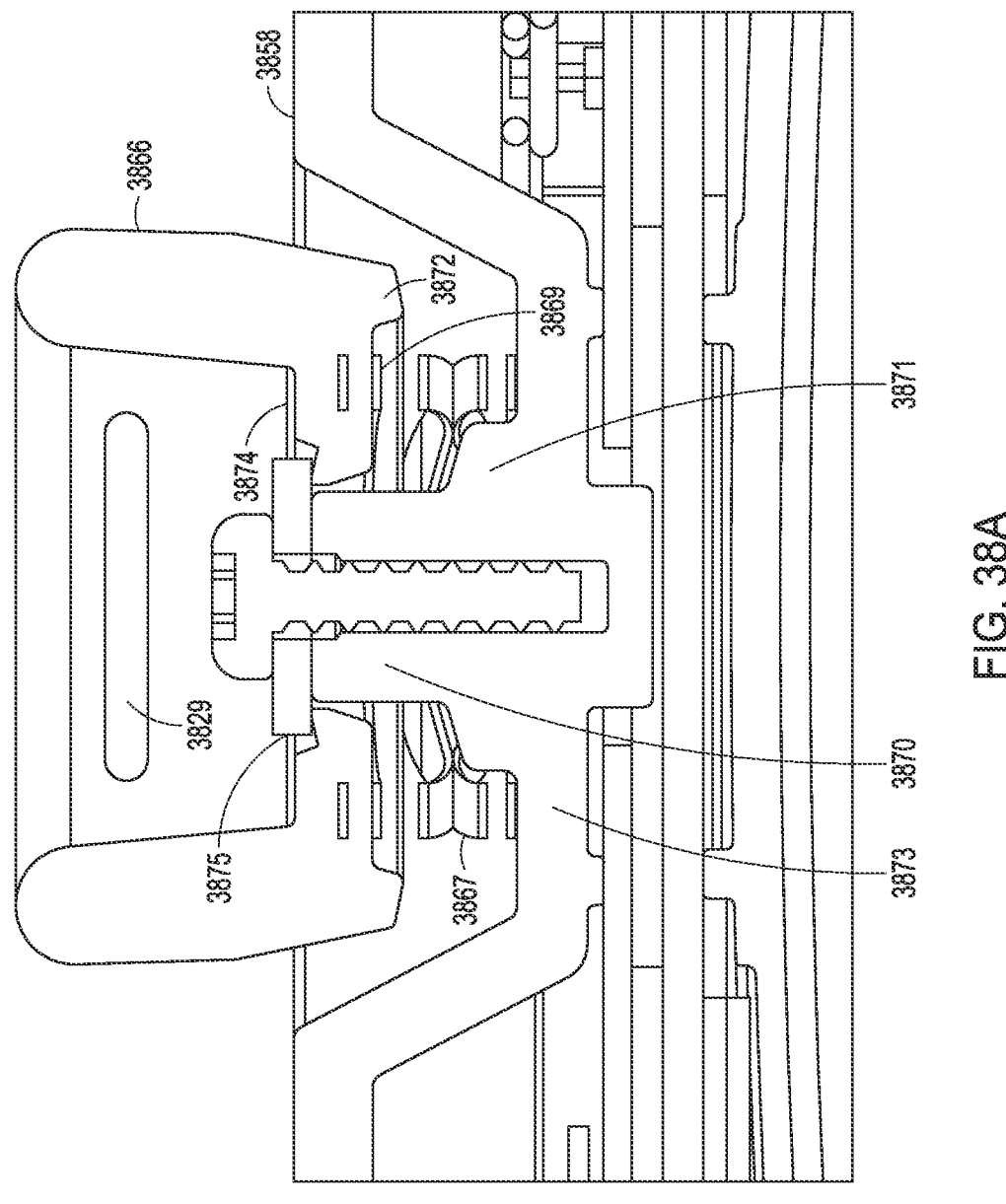
FIGS. 38A-38C illustrate allowable motion for a headset housing pivot with respect to the remainder of the completed coil assembly.
Figure 38B:
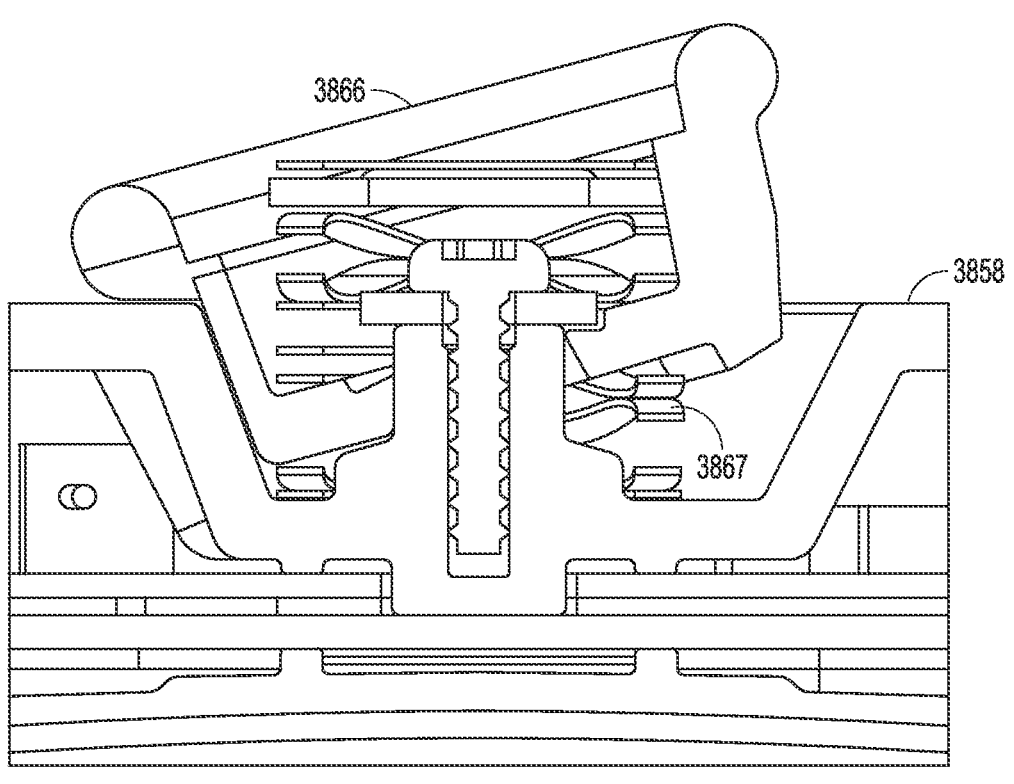
Figure 38C:
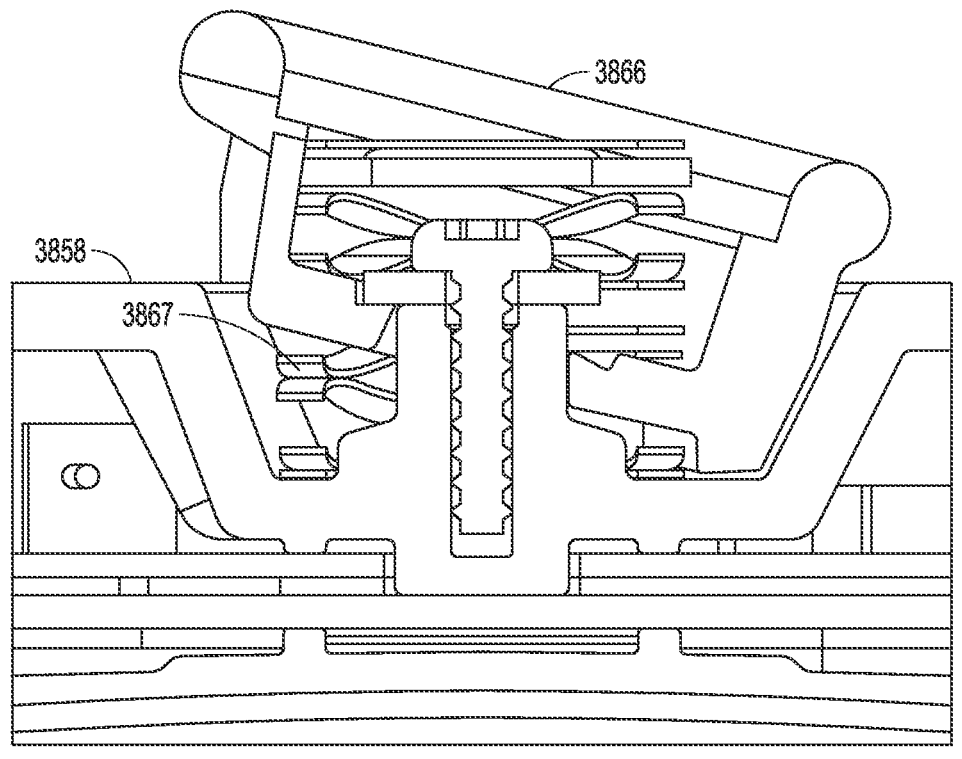

FIGS. 38A-38C illustrate allowable motion for a headset housing pivot with respect to the remainder of the completed coil assembly. FIG. 38A illustrates the headset housing pivot in a neutral position. FIG. 38B illustrates the headset housing pivot in one tilted direction, and FIG. 38C illustrates the headset housing pivot in another tilted direction The spring 3867 applies a force between the outer coil housing 3858 and the headset housing pivot 3866. The headset housing pivot 3866 and outer coil housing 3858 have contours that allow the headset housing pivot 3866 to tilt a limited amount (e.g., about 15 degrees) in any direction. For example, the headset housing pivot may have a recessed bottom 3869, and a center post 3870 of the outer coil housing 3858, which has the threaded aperture, may have slopes 3871 that engage the recessed bottom 3869 of the headset housing pivot to limit motion. Also, tilt motion may be limited by the bottom edge 3872 of the headset housing portion contacting a floor 3873 of a cavity in the outer coil housing 3858. The headset housing pivot 3866 may have a cavity with a floor 3874 with sloped features 3875 to allow the washer to fit when the headset housing pivot is tilted. Thus, when an arm is fit within the slot 3829 of the headset housing pivot, the headset housing pivot provides similar to a ball joint, as the headset housing pivot allows limited motion (including rotational and angular/tilting motion) around the axis. This allows the coil to self-align to the patient's head.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A system, comprising:
a headset band configured to be worn on a head of a patient, the headset band including a first end and a second end, the headset band, when worn on the head, being configured for the first end to be on a first side of the head when the second end is on a second side of the head;
a first arm, including a connection portion rotatably connected to the headset band to rotate about an axis near the first end and a coil portion extending rearward from the connection portion when the headset band is worn on the head;
a second arm, including a connection portion rotatably connected to the headset band to rotate about an axis near the second end and a coil portion extending rearward from the connection portion when the headset band is worn on the head;
a first coil assembly connected to the coil portion of the first arm, wherein rotation of the first arm about the axis near the first end changes a vertical position of the first coil assembly along the first side of the head when the headset band is worn on the head;
a second coil assembly connected to the coil portion of the second arm, wherein rotation of the second arm about the axis near the second end changes a vertical position of the second coil assembly along the second side of the head when the headset band is worn on the head; and
at least one power supply electrically connected to the first coil assembly and the second coil assembly.

2. The system of claim 1, wherein the at least one power supply includes a charger device connected to the first coil assembly by a first set of conductors in a cable and connected to the second coil assembly by a second set of conductors in the cable.

3. The system of claim 2, wherein the charger device includes at least one indicator configured to indicate when the first coil assembly is operably aligned with a first implantable device and indicate when the second coil assembly is operably aligned with a second implantable device.

4. The system of claim 3, wherein the at least one indicator includes a first light and a second light on an exterior of the charger device, the first light corresponding to alignment of the first coil assembly and the second light corresponding to alignment of the second coil assembly.

5. The system of claim 3, wherein the system is configured to determine alignment based on reflected impedance.

6. The system of claim 3, wherein the system is configured to determine alignment based on communication capability with the first and second implantable devices.

7. The system of claim 1, wherein the headset band has a flexible arcuate shape and has an ability to retain shape, the headset band being configured to be expanded to further separate the first and second ends when the headset band is applied to the head and allow the ability to retain shape to provide opposing forces for the first and second ends toward the head.

8. The system of claim 1, wherein each of the first and second arms has a bend between the coil portion and the connection portion.

9. The system of claim 1, wherein each of the first and second arms is flexible and has an ability to retain shape.

10. The system of claim 9, wherein each of the first and second arms further has a temple portion, wherein the connection portion is between the temple portion and the coil portion.

11. The system of claim 10, wherein each of the first and second arms has a bend between the temple portion and the connection portion and a bend between the connection portion and the coil portion such that the first and second arms curve inward toward the head when worn on the head.

12. The system of claim 1, further comprising a first arm bracket and a second arm bracket, wherein the first arm bracket is configured to rotatably connect the first arm to the headset band and the second arm bracket is configured to rotatably connect the second arm to the headset band.

13. The system of claim 12, wherein each of the first and second arm brackets includes a first bracket end portion and a second bracket end portion and an aperture extending therethrough at the first bracket end portion for a fastener to extend through to connect to the headset band.

14. The system of claim 13, wherein the first bracket end portion includes a recess with the aperture extending through the recess, the arm bracket including a bearing configured to fit within the recess, the first bracket end portion including a feature in the recess to engage with a feature in the bearing to limit rotational motion of the arm.

15. The system of claim 13, further comprising a spring between the headset band and the first bracket end portion to provide some resistance to rotation with respect to the headset band.

16. The system of claim 13, wherein the second bracket end portion includes a pivot portion configured to pivot about a pivot pin at the second bracket end portion, wherein the second bracket end portion is configured to be attached to the connection portion of a respective one of the first and second arms.

17. The system of claim 16, wherein the second bracket end portion includes a stop pin configured to limit pivoting motion of the pivot portion about the pivot pin.

18. The system of claim 16, wherein each of the first and second arm brackets includes a spring configured to provide a force against the pivot portion.

19. The system of claim 1, wherein each of the first and second coil assemblies includes an outer coil housing ultra-sonically welded to an inner coil housing to form a coil housing, and includes a coil electrically connected to a printed circuit board assembly (PCBA) within the coil housing.

20. The system of claim 19, wherein each of the first and second coil assemblies includes a strain relief between the outer coil housing and the inner coil housing, the strain relief is configured to relieve strain for an electrically conducting cable, and combination of the outer coil housing, the inner coil housing and the strain relief provide a tongue and groove fit between the strain relief and each of the outer coil housing and the inner coil housing.

21. The system of claim 1, wherein each of the first and second coil assemblies has a concave surface directed toward the head when worn on the head, and the concave surface is configured to assist with alignment over an implantable medical device.

22. A system, comprising:
a headset band configured to be worn on a head of a patient, the headset band including a first end and a second end, the headset band, when worn on the head, being configured for the first end to be on a first side of the head when the second end is on a second side of the head;
a first arm rotatably connected to the headset band near the first end;
a second arm rotatably connected to the headset band near the second end;
a first coil assembly connected to the first arm;
a second coil assembly connected to the second arm; and
at least one power supply electrically connected to the first coil assembly and the second coil assembly,
wherein the first coil assembly and the first arm are configured for the first coil assembly to slide over an end of the first arm, and the second coil assembly and the second arm are configured for the second coil assembly to slide over an end of the second arm.

23. The system of claim 22, wherein the end of the first arm and the end of the second arm each have a bent end portion, wherein the bent end portion is sufficiently flexible to allow a user to apply force to intentionally slide a corresponding one of the first coil assembly and the second coil assembly past the bent end portion on or off of the corresponding arm, while the corresponding one of the first coil assembly and the second coil assembly remain in place under normal use.

24. The system of claim 22, wherein the end of the first arm and the end of the second arm each have a stopper configured to be removably attached to the end, wherein a corresponding one of the first coil assembly and the second coil assembly is able to slide over the end when the stopper is removed, and is not able to slide over the end when the stopper is attached.

25. A system, comprising:
a headset band configured to be worn on a head of a patient, the headset band including a first end and a second end, the headset band, when worn on the head, being configured for the first end to be on a first side of the head when the second end is on a second side of the head;
a first arm rotatably connected to the headset band near the first end;
a second arm rotatably connected to the headset band near the second end;
a first coil assembly connected to the first arm;
a second coil assembly connected to the second arm; and
at least one power supply electrically connected to the first coil assembly and the second coil assembly,
wherein each of the first and second coil assemblies includes a coil housing with a recessed central portion and a post, a spring around the post, and a headset housing pivot connected to the post, wherein the spring applies a force between the headset housing pivot and the coil housing, wherein the coil housing and the headset housing pivot are configured to allow limited tilting motion of the headset housing pivot on the post.

* * * * *